(12) United States Patent
Turberg et al.

(10) Patent No.: US 9,066,945 B2
(45) Date of Patent: Jun. 30, 2015

(54) ECTOPARASITICIDAL ACTIVE SUBSTANCE COMBINATIONS

(75) Inventors: Andreas Turberg, Haan (DE); Ulrich Görgens, Ratingen (DE); Hans-Georg Schwarz, Dorsten (DE); Stefan Werner, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 32 days.

(21) Appl. No.: 13/995,958

(22) PCT Filed: Dec. 19, 2011

(86) PCT No.: PCT/EP2011/073280
§ 371 (c)(1),
(2), (4) Date: Feb. 17, 2014

(87) PCT Pub. No.: WO2012/084852
PCT Pub. Date: Jun. 28, 2012

(65) Prior Publication Data
US 2014/0179623 A1    Jun. 26, 2014

(30) Foreign Application Priority Data
Dec. 21, 2010  (DE) .................. 10 2010 063 691

(51) Int. Cl.
| | | |
|---|---|---|
| A61K 45/06 | (2006.01) | |
| A61K 31/497 | (2006.01) | |
| A01N 43/60 | (2006.01) | |
| C07D 401/14 | (2006.01) | |
| C07D 403/04 | (2006.01) | |
| C07D 403/14 | (2006.01) | |
| C07D 405/14 | (2006.01) | |

(52) U.S. Cl.
CPC .............. *A61K 31/497* (2013.01); *A01N 43/60* (2013.01); *C07D 401/14* (2013.01); *C07D 403/04* (2013.01); *C07D 403/14* (2013.01); *C07D 405/14* (2013.01); *A61K 45/06* (2013.01)

(58) Field of Classification Search
USPC ........................ 514/28, 255.05, 250; 544/405
See application file for complete search history.

(56) References Cited

U.S. PATENT DOCUMENTS

| | | | |
|---|---|---|---|
| 7,872,036 B2 | 1/2011 | Toriyabe et al. | |
| 7,897,543 B2 | 3/2011 | Bretschneider et al. | |
| 8,084,452 B2 | 12/2011 | Jeschke et al. | |
| 8,106,212 B2 | 1/2012 | Jeschke et al. | |
| 8,138,213 B2 | 3/2012 | Mita et al. | |
| 8,268,754 B2 | 9/2012 | Mita et al. | |
| 8,367,707 B2 | 2/2013 | Goto et al. | |
| 8,513,260 B2 * | 8/2013 | Schwarz et al. ......... | 514/255.05 |
| 8,546,577 B2 | 10/2013 | Jeschke et al. | |
| 2010/0173948 A1 | 7/2010 | Lahm et al. | |
| 2011/0021539 A1 | 1/2011 | Schwarz et al. | |
| 2011/0257231 A1 | 10/2011 | Koyanagi et al. | |
| 2011/0306499 A1 | 12/2011 | Bretschneider et al. | |

FOREIGN PATENT DOCUMENTS

| | | |
|---|---|---|
| EP | 0382173 A2 | 8/1990 |
| EP | 0539588 A1 | 5/1993 |
| EP | 2248422 A1 | 11/2010 |
| JP | 2007091708 | 4/2007 |
| JP | 2008110971 | 5/2008 |
| JP | 2008133273 | 6/2008 |
| WO | 2005035486 A1 | 4/2005 |
| WO | 2007027842 A1 | 3/2007 |
| WO | 2007043677 A1 | 4/2007 |
| WO | 2007048733 A1 | 5/2007 |
| WO | 2007075459 A2 | 7/2007 |
| WO | 2007095229 A2 | 8/2007 |
| WO | 2007125984 A1 | 11/2007 |
| WO | 2007149134 A1 | 12/2007 |
| WO | 2008104503 A1 | 9/2008 |
| WO | 2008128711 A1 | 10/2008 |
| WO | 2009002809 A2 | 12/2008 |
| WO | 2009024541 A2 | 2/2009 |
| WO | 2009060015 A1 | 5/2009 |
| WO | 2009097992 A1 | 8/2009 |
| WO | 2009112275 A1 | 9/2009 |
| WO | 2010020522 A1 | 2/2010 |
| WO | 2010043315 A1 | 4/2010 |
| WO | 2010090344 A1 | 8/2010 |

OTHER PUBLICATIONS

Cossio-Bayugar et al., "Cytochrome P-4S0 Monooxygenase Gene Expression Supports a Multifactorial Origin for Acaricide Resistance in Ripicephalus microplus," Research Journal Parasitology, 2008, 3(2):59-66.

Foil et al., "Factors that influence the prevalence of acaricide resistance and tick-borne diseases," Veterinary Parasitology, 2004, 125:163-181.

Ozoe et al., "The antiparasitic isoxazoline A1443 is a potent blocker of insect ligand-gated chloride channels," Biochemical and Biophysical Research Communications, 2010, 391:744-749.

The Pesticide Manual, 14th Edition, British Crop Portection Council, 2006, cover sheet, iii, and 1278-1342.

Rosario-Cruz et al., "Genetic basis and impact of tick acaricide resistance," Frontiers in Bioscience, Jan. 1, 2009, 14:2657-2665.

* cited by examiner

Primary Examiner — Rei-Tsang Shiao

(57) ABSTRACT

The present application relates to active compound combinations of pyrazin-2-ylpyrazoles (component A) with at least one further ectoparasiticide or synergists (component B), and to products comprising such active compound combinations. These active compound combinations are suitable for controlling animal pests in the field of veterinary medicine.

23 Claims, No Drawings

ECTOPARASITICIDAL ACTIVE SUBSTANCE COMBINATIONS

The present application relates to active compound combinations of pyrazin-2-ylpyrazoles (component A) with at least one further ectoparasiticide or synergists (component B), and to products comprising such active compound combinations. These active compound combinations are suitable for controlling animal pests in the field of veterinary medicine.

WO 2007/048733A describes the use of aminopyrazoles for controlling phytopathogenic harmful fungi, which in a general manner also includes pyrazin-2-ylpyrazoles. The pyrazin-2-ylpyrazoles carry only hydrogen as substituent in the 3-position.

WO 2007/027842A discloses anilinopyrazoles which may be substituted in the 1-position of the pyrazole moiety by 2-pyrazines. This international application relates to pharmaceutical applications, in particular to the treatment of diabetes; an arthropodicidal action is not described.

The active compounds already known from the publications mentioned above have disadvantages in their application; in particular, they have only unsatisfactory insecticidal activity, if any. Moreover, for the known classes of active compounds resistance has already been observed in some applications (Veterinary Parasitology (2004) 125, 163-181; Research Journal Parasitology (2008) 3, 59-66; Frontiers in Bioscience (2009) 14, 2657-2665). Accordingly, there is a need for further insecticides and/or parasiticides.

The pyrazin-2-ylpyrazoles of the formula (I) given below are described in the parallel pending application PCT/EP2010/003060 (WO 2010/136145).

Accordingly, it is an object of the present invention to provide alternative insecticidal and/or parasiticidal products having, compared to the active compounds known from the prior art, improved activity and/or a broader activity spectrum, in particular in activity-enhancing combination with other ectoparasiticides and/or synergists known in the field of veterinary medicine.

The active compounds referred to in the present description by their common name are known, for example, from "The Pesticide Manual" 14th Ed., British Crop Protection Council 2006, and the website http://www.alanwood.net/pesticides.

It has now been found that active compound combinations comprising, as component A, certain pyrazin-2-ylpyrazoles and, as component B, a further ectoparasiticidally active compound, have very good ectoparasiticidal activities of veterinary relevance.

Accordingly, the invention relates to products comprising, as component A, a compound of the general formula (I)

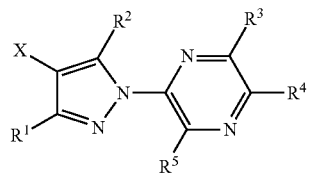

(I)

in which

X represents phenyl, 2-pyridyl or 3-pyridyl, each of which is substituted by one or more substituents selected from the group consisting of halogen, alkyl, haloalkyl, alkoxy, alkoxyalkyl, alkoxyalkoxy, cycloalkyl, alkenyloxy, alkynyloxy, benzyloxy, cycloalkylalkoxy, haloalkoxy, haloalkoxyalkyl, alkylsulphanyl, haloalkylsulphanyl, alkylsulphinyl, haloalkylsulphinyl, alkylsulphonyl, haloalkylsulphonyl, cyano, nitro, alkylcarbonyl, alkoxycarbonyl, alkoxycarbonylalkyl, carboxyl, carboxamide, dialkylcarboxamide, trialkylsilyl, amino, alkylamino, dialkylamino, alkylsulphonylamino, dialkylsulphonylamino, formyl, —CH=NO—H, —CH=NO-alkyl, —CH=NO-haloalkyl, —C(CH$_3$)=NO—H, —C(CH$_3$)=NO-alkyl, —C(CH$_3$)=NO-haloalkyl; and phenyl, 2-pyridyl and 3-pyridyl which are optionally substituted by one or more halogen atoms, cyano, nitro, alkyl, alkoxy or haloalkyl, where vicinal alkyl, haloalkyl, alkoxy and/or haloalkoxy groups at the phenyl substituent, 2-pyridyl substituent or 3-pyridyl substituent together with the carbon atoms to which they are attached may form a five- to six-membered cyclic system which contains 0 to oxygen or nitrogen atoms, where two oxygen atoms are not directly attached to one another, and whose alkyl moiety may optionally be substituted by one or more halogen atoms and/or further alkyl radicals, R$^1$ represents alkyl which is optionally monosubstituted or independently polysubstituted by alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, hydroxyl and/or cycloalkyl; alkenyl which is optionally monosubstituted or independently polysubstituted by halogen, alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl and/or cycloalkyl; cycloalkyl which is optionally monosubstituted or independently polysubstituted by alkyl, haloalkyl and/or halogen; haloalkyl which is optionally monosubstituted or independently polysubstituted by alkoxy, alkylsulphanyl, haloalkylsulphanyl, alkylsulphinyl, haloalkylsulphinyl, alkylsulphonyl, haloalkylsulphonyl and/or phenyl which is optionally monosubstituted or independently polysubstituted by halogen, alkyl, haloalkyl and/or alkoxy; phenyl which is optionally monosubstituted or independently polysubstituted by halogen, alkyl, haloalkyl and/or alkoxy; benzyl which is optionally monosubstituted or independently polysubstituted by halogen, alkyl, haloalkyl and/or alkoxy; cyano, formyl, alkylcarbonyl, —CH=NO—H, —CH=NO-alkyl, —CH=NO-haloalkyl, —C(CH$_3$)=NO—H, —C(CH$_3$)=NO-alkyl or —C(CH$_3$)=NO-haloalkyl, R$^2$ represents optionally substituted amino, where amino may be monosubstituted or independently disubstituted by alkyl, haloalkyl, alkoxyalkyl, alkylsulphanylalkyl, alkylsulphinylalkyl, alkylsulphonylalkyl, alkylcarbonyl, cycloalkyl, cycloalkylalkyl, alkenyl, where the radicals listed above are optionally substituted by halogen, cyano, alkoxy, alkoxycarbonyl and phenyl, where the phenyl ring is optionally mono- or polysubstituted by one or more substituents independently of one another selected from the group consisting of halogen, alkyl, haloalkyl and alkoxy; alkynyl, alkoxycarbonyl, alkenyloxycarbonyl, alkinyloxycarbonyl, alkoxycarbonylalkyl, alkoxycarbonylcarbonyl, heterocyclyl, heteroaryl, heterocyclylalkyl or heteroarylalkyl, where the heterocyclic or heteroaromatic ring may optionally be mono- or polysubstituted by one or more substituents independently of one another selected from the group consisting of halogen, alkyl, haloalkyl and alkoxy; benzyl or phenylcarbonyl, where the phenyl ring in benzyl and phenylcarbonyl is optionally mono- or polysubstituted by one or more substituents independently of one another selected from the group consisting of halogen, alkyl, haloalkyl and alkoxy, and R$^3$, R$^4$ independently of one another represent hydrogen, halogen, alkyl, cycloalkyl, haloalkyl, cyano, hydroxyl, formyl, alkylcarbonyl, —CH=NO—H, —CH=NO-alkyl, —CH═NO-haloalkyl, —C(CH₃)═NO—H, —C(CH₃)═NO-alkyl, —C(CH₃)═NO-haloalkyl, nitro, hydroxyl, SH, alkoxy, alkylsulphanyl, haloalkylsulphanyl, alkylsulphinyl, haloalkylsulphinyl, alkylsulphonyl or haloalkylsulphonyl, $R^5$ represents halogen, alkyl, haloalkyl, hydroxyl, alkoxy, alkoxyalkyl, alkoxyalkoxy, cycloalkyl, alkenyloxy, alkynyloxy, benzyloxy, cycloalkylalkoxy, haloalkoxy, haloalkoxyalkyl, —SH, alkylsulphanyl, haloalkylsulphanyl, alkylsulphinyl, haloalkylsulphinyl, alkylsulphonyl, haloalkylsulphonyl, cyano, nitro, alkylcarbonyl, alkoxycarbonyl, alkoxycarbonylalkyl, carboxyl, carboxamide, dialkylcarboxamide, trialkylsilyl, amino, alkylamino, dialkylamino, alkylsulphonylamino, dialkylsulphonylamino, formyl, —CH═NO—H, —CH═NO-alkyl, —CH═NO-haloalkyl, —C(CH₃)═NO—H, —C(CH₃)═NO-alkyl, —C(CH₃)═NO-haloalkyl, heteroaryl, where the heteroaromatic ring may optionally be mono- or polysubstituted by one or more substituents independently of one another selected from the group consisting of halogen, alkyl, haloalkyl and alkoxy, or N-oxides or salts thereof, and, as component B, an active compound of the following active compound groups I-1 to I-25: (I-1) acetylcholinesterase (AChE) inhibitors; (I-2) GABA-gated chloride channel antagonists; (I-3) sodium channel modulators/voltage-dependent sodium channel blockers; (I-4) nicotinergic acetylcholine receptor agonists; (I-5) allosteric acetylcholine receptor modulators (agonists); (I-6) chloride channel activators; (I-7) juvenile hormone analogues; (I-8) mite growth inhibitors; (I-9) Slo-1 and latrophilin receptor agonists; (I-10) oxidative phosphorylation inhibitors, ATP disruptors; (I-11) oxidative phosphorylation decouplers acting by interrupting the H proton gradient; (I-12) nicotinergic acetylcholine receptor antagonists; (I-13) chitin biosynthesis inhibitors, type 0; (I-14) chitin biosynthesis inhibitors, type 1; (I-15) moulting disruptors; (I-16) ecdysone agonists/disruptors; (I-17) octopaminergic agonists; (I-18) complex-III electron transport inhibitors; (I-19) complex-I electron transport inhibitors; (I-20) voltage-dependent sodium channel blockers; (I-21) inhibitors of acetyl-CoA carboxylase; (I-22) complex-II electron transport inhibitors; (I-23) ryanodine receptor effectors; (I-24) further active compounds with unknown mechanism of action, such as, for example, benzoximate, chinomethionat, cyflumetofen, pyridalyl, sulfoxaflor, penigequinolone A; (I-25) synergists such as MGK264 and piperonyl butoxide (PBO).

Preferred embodiments with respect to the compounds of the general formula (I) are described below:

In a first embodiment of the present invention, compounds of the general formula (I)

(a) are preferred in which the radical X represents phenyl, 2-pyridyl or 3-pyridyl, each of which is substituted by one or more substituents selected from the group consisting of halogen, alkyl, haloalkyl, alkoxy, haloalkoxy, alkylsulphanyl, haloalkylsulphanyl, alkylsulphinyl, haloalkylsulphinyl, alkylsulphonyl, haloalkylsulphonyl, cyano, nitro, dialkylamino; and phenyl, 2-pyridyl and 3-pyridyl which are optionally substituted by one or more halogen atoms, cyano, nitro, alkyl, alkoxy or haloalkyl, where vicinal alkyl, haloalkyl and/or alkoxy groups at the phenyl substituent, 2-pyridyl substituent or 3-pyridyl substituent together with the carbon atoms to which they are attached may form a five- to six-membered cyclic system which contains 0 to 2 oxygen or nitrogen atoms, where two oxygen atoms are not directly attached to one another, and whose alkyl moiety may optionally be substituted by one or more halogen atoms and/or further alkyl radicals;

(b) are more preferred in which the radical X represents phenyl, 2-pyridyl or 3-pyridyl, each of which is substituted by one or more substituents selected from the group consisting of halogen, alkyl, haloalkyl, alkoxy, haloalkoxy, alkylsulphanyl, haloalkylsulphanyl, alkylsulphinyl, haloalkylsulphinyl, alkylsulphonyl, haloalkylsulphonyl, cyano and dialkylamino; and phenyl, 2-pyridyl and 3-pyridyl which are optionally substituted by one or more halogen atoms, cyano, nitro, alkyl, alkoxy or haloalkyl, where vicinal alkyl, haloalkyl and/or alkoxy groups at the phenyl substituent, 2-pyridyl substituent or 3-pyridyl substituent together with the carbon atoms to which they are attached may form a five- to six-membered cyclic system which contains 1 or 2 oxygen atoms, where two oxygen atoms are not directly attached to one another, and whose alkyl moiety may optionally be substituted by one or more halogen atoms and/or further alkyl radicals;

(c) are particularly preferred in which the radical X represents phenyl, 2-pyridyl or 3-pyridyl, each of which is substituted by one or more substituents selected from the group consisting of fluorine, chlorine, bromine, iodine, $CF_3$, methoxy, ethoxy, trifluoroethoxy, methylsulphanyl, 2,2,2-trifluoro-ethylsulphanyl, methylsulphinyl, 2,2,2-trifluoroethyl-sulphinyl, methylsulphonyl, 2,2,2-trifluoroethyl-sulphonyl, cyano and dimethylamino; and phenyl which is optionally substituted by one or more halogen atoms, cyano, nitro, methyl, methoxy or $CF_3$, where vicinal alkyl or alkoxy groups at the phenyl substituent together with the carbon atoms to which they are attached may form a five- to six-membered cyclic system which contains 1 or 2 oxygen atoms, where two oxygen atoms are not directly attached to one another, and whose alkyl moiety may be substituted by one or more further alkyl radicals;

(d) are very particularly preferred in which the radical X represents phenyl which is substituted at up to three carbon atoms by substituents selected from the group consisting of chlorine, alkoxy having up to 4 carbon atoms (for example methoxy or ethoxy), di($C_{1-4}$)-alkylamino (for example dimethylamino) and the group —O—CH₂—O— attached via the oxygen atoms to two vicinal carbon atoms of the phenyl ring; for example, X represents 7-chloro-1,3-benzodioxol-5-yl-; 3,5-dichloro-4-methoxyphenyl; 3,5-dichloro-4-dimethylaminophenyl.

In a second embodiment of the present invention, compounds of the general formula (I)

(a) are preferred in which the radical $R^1$ represents alkyl which is optionally monosubstituted or independently polysubstituted by alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, hydroxyl and/or cycloalkyl; alkenyl which is optionally monosubstituted or independently polysubstituted by halogen, alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl and/or cycloalkyl; cycloalkyl which is optionally monosubstituted or independently polysubstituted by alkyl, haloalkyl and/or halogen; haloalkyl which is optionally monosubstituted or independently polysubstituted by alkoxy, alkylsulphanyl, haloalkylsulphanyl, alkylsulphinyl, haloalkylsulphinyl, alkylsulphonyl, haloalkylsulphonyl and/or phenyl; CH═NOH, CH═NOCH₃ and CN;

(b) are more preferred in which the radical $R^1$ represents alkyl which is optionally monosubstituted or independently polysubstituted by alkoxy; alkenyl which is optionally monosubstituted or independently polysubstituted by halogen; cycloalkyl which is optionally monosubstituted or independently polysubstituted by alkyl, haloalkyl and/or halogen; haloalkyl which is optionally monosubstituted or independently polysubstituted by alkoxy; CH=NOH, CH=NOCH$_3$ and CN;

(c) are particularly preferred in which the radical R$^1$ represents CH$_3$, CH$_2$CH$_3$, CH(CH$_3$)$_2$, CH$_2$CH$_3$CH$_3$, C(CH$_3$)$_3$, C(OCH$_3$)HCH$_2$CH$_3$, CH(OCH$_3$)$_2$, CH=CH$_2$, prop-1-en-2-yl, cyclopropyl, CF$_3$, CHFCH$_3$, CHF$_2$, CF$_2$Cl, CF$_2$Br, CF$_2$CF$_3$, CF$_2$CH$_3$, CF$_2$CF$_2$CF$_3$, CF$_2$CF$_2$H, CH=NOH, CH=NOCH$_3$ and CN;

(d) are very particularly preferred in which the radical R$^1$ represents CF$_3$.

In a third embodiment of the present invention, compounds of the general formula (I) are preferred in which the radical R$^2$ represents amino and substituted amino, where the substituted amino may be monosubstituted or independently disubstituted by alkyl, haloalkyl, cycloalkylalkyl, optionally halogen- or phenyl-substituted alkenyl, alkynyl, heterocyclylalkyl and/or heteroarylalkyl, where the heteroaromatic ring may optionally be mono- or polysubstituted by one or more substituents independently of one another selected from the group consisting of halogen, alkyl, haloalkyl and alkoxy; benzyl, where the phenyl ring in benzyl may optionally be mono- or polysubstituted by one or more substituents independently of one another selected from the group consisting of halogen, alkyl, haloalkyl and alkoxy;

(a) are more preferred in which the radical R$^2$ represents amino and substituted amino, where the substituted amino may be monosubstituted or independently disubstituted by alkyl, optionally halogen- or phenyl-substituted alkenyl, alkynyl, heteroarylalkyl, where the heteroaromatic ring may optionally be mono- or polysubstituted by one or more substituents independently of one another selected from the group consisting of halogen and/or alkyl; benzyl, where the phenyl ring in benzyl may optionally be mono- or polysubstituted by one or more substituents independently of one another selected from the group consisting of halogen and alkoxy;

(b) are particularly preferred in which the radical R$^2$ represents amino, methylamino, dimethylamino, benzylamino, dibenzylamino, (4-chlorobenzyl)amino, bis(4-chlorobenzyl)amino, (4-methoxybenzyl)amino, bis(4-methoxybenzyl)amino, (2-methylprop-2-en-1-yl)amino, prop-2-en-1-ylamino, prop-2-yn-1-ylamino, bis(prop-2-yn-1-yl)amino, (pyrazin-2-ylmethyl)amino, (6-methylpyridin-2-ylmethyl)amino, bis(6-methylpyridin-2-ylmethyl)amino and (pyridin-2-ylmethyl)amino; from among these in turn the radical R$^2$ particularly preferably represents amino (—NH$_2$).

In a fourth embodiment of the present invention, compounds of the general formula (I)

(a) are preferred in which the radicals R$^3$ and R$^4$ independently of one another represent hydrogen, halogen, alkyl, cycloalkyl, haloalkyl, cyano and/or hydroxyl;

(b) are more preferred in which the radicals R$^3$ and R$^4$ independently of one another represent hydrogen, halogen and/or alkyl;

(c) are particularly preferred in which the radicals R$^3$ and R$^4$ independently of one another represent hydrogen, chlorine and/or methyl;

(d) are very particularly preferred in which the radicals R$^3$ and R$^4$ represent hydrogen.

In a fifth embodiment of the present invention, compounds of the general formula (I)

(a) are preferred in which the radical R$^5$ represents halogen, alkyl, haloalkyl, hydroxyl, alkoxy, haloalkoxy, alkylsulphanyl, haloalkylsulphanyl, alkylsulphinyl, haloalkylsulphinyl, alkylsulphonyl, haloalkylsulphonyl, cyano, amino, alkylamino, dialkylamino, alkylsulphonylamino, dialkylsulphonylamino, heteroaryl, where the heteroaromatic ring may optionally be mono- or polysubstituted by one or more substituents independently of one another selected from the group consisting of halogen, alkyl, haloalkyl and alkoxy;

(b) are more preferred in which the radical R$^5$ represents halogen, alkyl, haloalkyl, alkoxy, haloalkoxy, alkylsulphanyl, alkylsulphinyl, haloalkylsulphinyl, alkylsulphonyl, cyano, dialkylamino or heteroaryl, where the heteroaromatic ring may optionally be mono- or polysubstituted by one or more substituents independently of one another selected from the group consisting of halogen and alkyl; and (c) are particularly preferred in which the radical R$^5$ represents chlorine, bromine, methyl, CF$_3$, methoxy, ethoxy, propoxy, propan-2-yloxy, dimethylamino, cyano, methylsulphanyl, methylsulphinyl, methylsulphonyl, 1H-pyrazol-1-yl, 1H-imidazol-1-yl and 4-fluoro-1H-pyrazol-1-yl;

(d) are very particularly preferred in which the radical R$^5$ represents methoxy or in particular ethoxy.

In the context of the present invention, the compound of the general formula (I) also comprises compounds which are quarternized at a nitrogen atom by a) protonation, b) alkylation or c) oxidation.

By addition of a suitable inorganic or organic acid such as, for example, HCl, HBr, H$_2$SO$_4$ or HNO$_3$, or else oxalic acid or sulphonic acids, onto a basic group such as, for example, amino or alkylamino, the compounds of the general formula (I) may form salts. Suitable substituents such as, for example, sulphonic acids or carboxylic acids, which are present in deprotonated form, may form inner salts with groups which for their part can be protonated, such as amino groups. Salts may also be formed by replacing the hydrogen of suitable substituents, such as, for example, sulphonic acids or carboxylic acids, by a pharmaceutically suitable cation. These salts are, for example, metal salts, in particular alkali metal salts or alkaline earth metal salts, especially sodium salts and potassium salts, or else ammonium salts, salts with organic amines or quartary ammonium salts having cations of the formula [NRR'R''R''']+ in which R to R''' each independently represent an organic radical, in particular alkyl, aryl, aralkyl or alkylaryl.

In the general formula (I) and all other formulae in the present invention, the radicals alkyl, alkoxy, haloalkyl, haloalkoxy, alkylamino, alkylsulphinyl and alkylsulphonyl, and the corresponding unsaturated and/or substituted radicals may in each case be straight-chain or branched in the hydrocarbon skeleton. Unless specifically indicated, in these radicals the lower carbon skeletons having, for example, 1 to 6 carbon atoms, in particular 1 to 4 carbon atoms, or in the case of unsaturated groups 2 to 6 carbon atoms, in particular 2 to 4 carbon atoms, are preferred. Alkyl radicals, including in the composite meanings such as alkoxy, haloalkyl etc., are, for example, methyl; ethyl; propyl such as n- or isopropyl; butyl such as n-, i-, t- or 2-butyl; pentyl such as n-pentyl, isopentyl and neopentyl; hexyl such as n-hexyl, isohexyl, 3-methylpentyl, 2,2-dimethylbutyl and 2,3-dimethylbutyl; and heptyl such as n-heptyl, 1-methylhexyl and 1,4-dimethylpentyl; alkenyl and alkynyl radicals have the meaning of the possible unsaturated radical which correspond to the alkyl radicals and contain at least one double or triple bond, preferably one double bond or triple bond. Alkenyl is, for example, vinyl, 1-allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, ethynyl, propargyl/propynyl, but-2-yn-1-yl, but-3-yn-1-yl and 1-methylbut-3-yn-1-yl.

Cycloalkyl groups are, for example, cyclopropyl, cyclobutyl, cyclopentyl, cyclohexyl, cycloheptyl and cyclooctyl. The cycloalkyl groups may be in bi- or tricyclic form.

If haloalkyl groups and haloalkyl radicals of haloalkoxy, haloalkenyl, haloalkynyl etc. are stated, for these radicals the lower carbon skeleton having, for example, 1 to 6 carbon atoms or 2 to 6, in particular 1 to 4, carbon atoms or preferably 2 to 4 carbon atoms, and also the corresponding unsaturated and/or substituted radicals are in each case straight-chain or branched in the carbon skeleton. Examples are trifluoromethyl, difluoromethyl, 2,2,2-trifluoroethyl, trifluoroallyl and 1-chloroprop-1-yl-3-yl.

In these radicals, alkylene groups are the lower carbon skeletons having, for example, 1 to 10 carbon atoms, in particular 1 to 6 carbon atoms or preferably 2 to 4 carbon atoms, and also the corresponding unsaturated and/or substituted radicals in the carbon skeleton, which may in each case be straight-chain or branched. Examples are methylene, ethylene, n- and isopropylene and n-, s-, iso-, t-butylene.

In these radicals, hydroxyalkyl groups are the lower carbon skeletons having, for example, 1 to 6 carbon atoms, in particular 1 to 4 carbon atoms, and also the corresponding unsaturated and/or substituted radicals in the carbon skeleton, which may in each case be straight-chain or branched. Examples are 1,2-dihydroxyethyl and 3-hydroxypropyl.

Halogen is fluorine, chlorine, bromine or iodine, haloalkyl, -alkenyl and -alkynyl mean alkyl, alkenyl and alkynyl, respectively, partially or fully substituted by halogen, preferably by fluorine, chlorine or bromine, in particular by fluorine and/or chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

Aryl is a mono-, bi- or polycyclic aromatic system, for example phenyl or naphthyl, preferably phenyl.

A heterocyclic radical (heterocyclyl) contains at least one heterocyclic ring (=carbocyclic ring in which at least one carbon atom is replaced by a heteroatom, preferably by a heteroatom from the group consisting of N, O, S, P, B, Si, Se) which is saturated, unsaturated or heteroaromatic and may be unsubstituted or substituted, where the binding site is located at a ring atom.

If the heterocyclyl radical or the heterocyclic ring is optionally substituted, it may be fused with other carbocyclic or heterocyclic rings. Optionally substituted heterocyclyl also includes polycyclic systems such as, for example, 8-azabicyclo[3.2.1]octanyl or 1-azabicyclo[2.2.1]heptyl. Optionally substituted heterocyclyl also includes spirocyclic systems such as, for example, 1-oxa-5-azaspiro[2.3]hexyl.

Unless defined otherwise, the heterocyclic ring contains preferably 3 to 9 ring atoms, in particular 3 to 6 ring atoms and one or more, preferably 1 to 4, in particular 1, 2 or 3, heteroatoms in the heterocyclic ring, preferably from the group consisting of N, O, and S; however, two oxygen atoms must not be directly adjacent.

In the context of the present invention, the term heteroaryl is to be understood like systems defined above under "heterocyclyl"; however, these systems are heteroaromatic, i.e. represent a completely unsaturated aromatic heterocyclic compound.

Unless defined otherwise, the definition "substituted by one or more radicals" refers independently of one another to one or more identical or different radicals, where two or more radicals at a cycle as basic structure may form one or more rings Substituted radicals, such as a substituted alkyl, alkenyl, alkynyl, cycloalkyl, cycloalkenyl, aryl, phenyl, benzyl, heterocyclyl and heteroaryl radical, refer, for example, to a substituted radical derived from an unsubstituted basic structure, where the substituents are, for example, one or more, preferably 1, 2 or 3, radicals from the group consisting of halogen, alkoxy, alkylthio, hydroxyl, amino, nitro, carboxyl or a group equivalent to the carboxyl group, cyano, isocyanato, azido, alkoxycarbonyl, alkylcarbonyl, formyl, carbamoyl, mono- and dialkylaminocarbonyl, substituted amino, such as acylamino, mono- and dialkylamino, trialkylsilyl and optionally substituted cycloalkyl, optionally substituted aryl, optionally substituted heterocyclyl, where each of the lastmentioned cyclic groups may also be attached via heteroatoms or divalent functional groups as in the case of the alkyl radicals mentioned, and alkylsulphinyl, which includes both enantiomers of the alkylsulphonyl group, alkylsulphonyl, alkylphosphinyl, alkylphosphonyl and, in the case of cyclic radicals (="cyclic basic structure"), also alkyl, haloalkyl, alkylthioalkyl, alkoxyalkyl, optionally substituted mono- and dialkylaminoalkyl and hydroxyalkyl; the term "substituted radicals" such as substituted alkyl etc. includes as substituents in addition to the saturated hydrocarbon-containing radicals mentioned corresponding unsaturated aliphatic and aromatic radicals, such as optionally substituted alkenyl, alkynyl, alkenyloxy, alkynyloxy, alkenylthio, alkynylthio, alkenyloxycarbonyl, alkynyloxycarbonyl, alkenylcarbonyl, alkynylcarbonyl, mono- and dialkenylaminocarbonyl, mono- and dialkynylaminocarbonyl, mono- and dialkenylamino, mono- and dialkynylamino, trialkenylsilyl, trialkynylsilyl, optionally substituted cycloalkenyl, optionally substituted cycloalkynyl, phenyl, phenoxy etc. In the case of substituted cyclic radicals having aliphatic moieties in the ring, this also includes cyclic systems having substituents which are attached to the ring via a double bond, for example substituted by an alkylidene group such as methylidene or ethylidene or an oxo group, imino group or substituted imino group.

If two or more radicals form one or more rings, these may be carbocyclic, heterocyclic, saturated, partially saturated, unsaturated, for example also aromatic and optionally substituted further. The fused rings are preferably 5- or 6-membered rings, benzo-fused cycles being particularly preferred.

The substituents mentioned in an exemplary manner ("first substituent level") may, if they comprise hydrocarbon-containing moieties, optionally be further substituted therein ("second substituent level"), for example by one of the substituents as defined for the first substituent level. Corresponding further substituent levels are possible. Preferably, the term "substituted radicals" only includes one or two substituent levels.

Preferred substituents for the substituent levels are, for example, amino, hydroxyl, halogen, nitro, cyano, isocyano, mercapto, isothiocyanato, carboxyl, carbonamide, $SF_5$, aminosulphonyl, alkyl, cycloalkyl, alkenyl, cycloalkenyl, alkynyl, monoalkylamino, dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulphenyl, alkylsulphinyl, which includes both enantiomers of the alkylsulphinyl group, alkylsulphonyl, monoalkyl-aminosulphonyl, dialkylaminosulphonyl, alkylphosphinyl, alkylphosphonyl, where alkylphosphinyl and alkylphosphonyl include both enantiomers, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino, benzylamino, heterocyclyl and trialkylsilyl.

As already mentioned, in the case of radicals having carbon atoms preference is given to those having 1 to 6 carbon atoms, preferably 1 to 4 carbon atoms, in particular 1 or 2 carbon atoms. Preference is generally given to substituents from the group consisting of halogen, for example fluorine, chlorine and bromine, (C1-C4)-alkyl, preferably methyl or ethyl, (C1-C4)-haloalkyl, preferably trifluoromethyl, (C1-C4)-alkoxy, preferably methoxy or ethoxy, (C1-C4)-haloalkoxy, nitro and cyano.

Optionally substituted aryl or heteroaryl is preferably phenyl or heteroaryl which is unsubstituted or mono- or polysubstituted, preferably up to trisubstituted, by identical or different radicals from the group consisting of halogen, (C1-C4)-alkyl, (C3-C6)-cycloalkyl, (C1-C4)-alkoxy, (C1-C4)-haloalkyl, (C1-C4)-haloalkoxy, (C1-C4)-alkylthio, cyano and nitro, for example o-, m- and p-tolyl, di-methylphenyls, 2-, 3- and 4-chlorophenyl, 2-, 3- and 4-trifluoromethyl and 2-, 3- and 4-trichloromethylphenyl, 2,4-, 3,5-, 2,5- and 2,3-dichlorophenyl, o-, m- and p-methoxyphenyl.

If appropriate. the compounds according to the invention may be present as mixtures of different possible isomeric forms, in particular of stereoisomers, such as, for example, E and Z, threo and erythro, and also optical isomers, and, if appropriate, also of tautomers. What is claimed are both the E and the Z isomers, and also the threo and erythro as well as the optical isomers, any mixtures of these isomers, and the possible tautomeric forms.

The compounds of Table 1 below may be mentioned as particularly preferred examples of the active compounds of component A:

TABLE 1

| | |
|---|---|
| A-1 | 4-(7-chloro-1,3-benzodioxol-5-yl)-1-(3-ethoxypyrazin-2-yl)-3-(trifluoromethyl)-1H-pyrazole-5-amine |
| A-2 | 4-(7-chloro-1,3-benzodioxol-5-yl)-1-(3-methoxypyrazin-2-yl)-3-(trifluoromethyl)-1H-pyrazole-5-amine |
| A-3 | 4-(7-chloro-1,3-benzodioxol-5-yl)-1-(3-methoxypyrazin-2-yl)-3-methyl-1H-pyrazole-5-amine |
| A-4 | 4-(7-chloro-1,3-benzodioxol-5-yl)-1-(3-ethoxypyrazin-2-yl)-3-ethyl-1H-pyrazole-5-amine |
| A-5 | 4-(7-chloro-1,3-benzodioxol-5-yl)-1-(3-methoxypyrazin-2-yl)-3-ethyl-1H-pyrazole-5-amine |
| A-6 | 4-(7-chloro-1,3-benzodioxol-5-yl)-1-(3-methoxypyrazin-2-yl)-3-isopropyl-1H-pyrazole-5-amine |
| A-7 | 4-(7-chloro-1,3-benzodioxol-5-yl)-1-(3-methoxypyrazin-2-yl)-3-cyclopropyl-1H-pyrazole-5-amine |
| A-8 | 4-(7-bromo-1,3-benzodioxol-5-yl)-1-(3-ethoxypyrazin-2-yl)-3-(trifluoromethyl)-1H-pyrazole-5-amine |
| A-9 | 4-(7-bromo-1,3-benzodioxol-5-yl)-1-(3-methoxypyrazin-2-yl)-3-(trifluoromethyl)-1H-pyrazole-5-amine |
| A-10 | 4-(7-bromo-1,3-benzodioxol-5-yl)-1-(3-ethoxypyrazin-2-yl)-3-ethyl-1H-pyrazole-5-amine |
| A-11 | 4-(7-bromo-1,3-benzodioxol-5-yl)-1-(3-methoxypyrazin-2-yl)-3-ethyl-1H-pyrazole-5-amine |
| A-12 | 1-(3-ethoxypyrazin-2-yl)-3-(triluoromethyl)-4-[7-(trifluoromethyl)-1,3-benzodioxol-5-yl]-1H-pyrazole-5-amine |
| A-13 | 1-(3-methoxypyrazin-2-yl)-3-(triluoromethyl)-4-[7-(trifluoromethyl)-1,3-benzodioxol-5-yl]-1H-pyrazole-5-amine |
| A-14 | 4-(3,5-dichloro-4-methoxyphenyl)-1-(3-ethoxypyrazin-2-yl)-3-(trifluoromethyl)-1H-pyrazole-5-amine |
| A-15 | 4-[3,5-dichloro-4-(dimethylamino)phenyl]-1-(3-ethoxypyrazin-2-yl)-3-(trifluoromethyl)-1H-pyrazole-5-amine |

TABLE 2

Analytical characterization of the examples from Table 1

| | |
|---|---|
| A-1 | $^1$H NMR (400 MHz, DMSO-d6), δ 8.43 (d, 1H), 8.24 (d, 1H), 6.84 (s, 2H), 6.18 (s, 2H), 5.78 (s, 2H), 4.47 (q, 2H), 1.32 (t, 3H). |
| A-2 | $^1$H-NMR (400 MHz, DMSO-d6), δ 4.00 (s, 3H), 5.60 (bs, 2H), 6.15 (s, 2H), 6.83-6.84 (m, 2H), 8.24 (d, 1H), 8.42 (d, 1H). |
| A-3 | $^1$H NMR (400 MHz, DMSO-d6), δ 8.27 (d, 1H), 8.15 (d, 1H), 6.87 (s, 1H), 6.84 (s, 1H), 6.11 (s, 2H), 5.21 (bs, 2H, NH$_2$), 3.96 (s, 3H), 2.11 (s, 3H). |
| A-4 | $^1$H NMR (400 MHz, DMSO-d6), δ 8.27 (d, 1H), 8.16 (d, 1H), 6.88 (s, 1H), 6.84 (s, 1H), 6.14 (s, 2H), 5.30 (bs, 2H, NH$_2$), 4.44 (q, 2H), 2.53 (q, 2H), 1.33 (t, 3H), 1.08 (t, 3H). |
| A-5 | $^1$H NMR (400 MHz, DMSO-d6), δ 8.28 (d, 1H), 8.16 (d, 1H), 6.85 (s, 1H), 6.82 (s, 1H), 6.12 (s, 2H), 5.14 (bs, 2H, NH$_2$), 3.97 (s, 3H), 2.56-2.49 (q, 2H), 1.08 (t, 3H). |
| A-6 | $^1$H NMR (400 MHz, DMSO-d6), δ 8.31 (d, 1H), 8.18 (d, 1H), 6.85 (s, 1H), 6.82 (s, 1H), 6.15 (s, 2H), 5.21 (bs, 2H, NH$_2$), 3.96 (s, 3H), 2.98-2.93 (m, 1H), 1.11 (d, 3H). |
| A-7 | $^1$H NMR (400 MHz, DMSO-d6), δ 8.31 (d, 1H), 8.17 (d, 1H), 6.98 (s, 1H), 6.95 (s, 1H), 6.14 (s, 2H), 5.34 (bs, 2H, NH$_2$), 3.97 (s, 3H), 1.77-1.73 (m, 1H), 0.81-0.73 (m, 4 H). |
| A-8 | $^1$H NMR (400 MHz, DMSO-d6), δ 8.43 (d, 1H), 8.24 (d, 1H), 6.94 (s, 1H), 6.86 (s, 1H), 6.17 (s, 2H), 5.79 (bs, 2H, NH$_2$), 4.47 (q, 2H), 1.32 (t, 3H). |
| A-9 | $^1$H NMR (400 MHz, DMSO-d6), δ 8.45 (d, 1H), 8.26 (d, 2H), 6.95 (s, 1H), 6.87 (s, 1H), 6.17 (s, 2H), 5.80 (s, 2H), 3.98 (s, 3H). |
| A-10 | $^1$H NMR (400 MHz, DMSO-d6), δ 8.28 (d, 1H), 8.16 (d, 1H), 6.94 (s, 1H), 6.90 (s, 1H), 6.13 (s, 2H), 5.30 (bs, 2H, NH$_2$), 4.44 (q, 2H), 2.53 (q, 2H), 1.33 (t, 3H), 1.08 (t, 3H). |
| A-11 | $^1$H NMR (400 MHz, DMSO-d6), δ 8.31 (d, 1H), 8.18 (d, 1H), 6.94 (s, 1H), 6.90 (s, 1H), 6.13 (s, 2H), 5.30 (bs, 2H, NH$_2$), 3.96 (s, 3H), 2.52 (q, 2H), 1.06 (t, 3H). |
| A-12 | $^1$H NMR (400 MHz, DMSO-d6), δ 8.44 (d, 1H), 8.25 (d, 1H), 7.14 (s, 1H), 6.99 (s, 1H), 6.26 (s, 2H), 5.86 (bs, 2H, NH$_2$), 4.48 (q, 2H), 1.32 (t, 3H). |
| A-13 | $^1$H NMR (400 MHz, DMSO-d6), δ 8.47 (d, 1H), 8.28 (d, 1H), 7.15 (s, 1H), 6.99 (s, 1H), 6.26 (s, 2H), 5.86 (bs, 2H, NH$_2$), 3.99 (s, 3H). |
| A-14 | $^1$H NMR (400 MHz, DMSO-d6), δ 8.44 (d, 1H), 8.26 (d, 1H), 7.40 (s, 2H), 5.98 (bs, 2H, NH$_2$), 4.48 (q, 2H), 3.87 (s, 3H), 1.32 (t, 3H). |
| A-15 | $^1$H NMR (400 MHz, DMSO-d6), δ 8.44 (d, 1H), 8.25 (d, 1H), 7.33 (s, 2H), 5.97 (bs, 2H, NH$_2$), 4.47 (q, 2H), 2.86 (s, 6H), 1.32 (t, 3H). |

The pyrazin-2-ylpyrazoles of the formula (I) (component A) and their preparation are described in the application PCT/EP2010/003060 (laid open as WO2010/136145). A-14 and A-15 are not explicitly mentioned therein, but are embraced by formula (I) and can be prepared analogously to the process described therein. Thus, A-14 can be prepared from (3,5-dichloro-4-methoxyphenyl)acetonitrile by the process described therein. The preparation of A-15 is described in detail in the examples.

Component B comprises one or more compounds of groups (I-1) to (I-25).

(I-1) Acetylcholinesterase (AChE) inhibitors, such as, for example, carbamates, for example, alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb;

bendiocarb, carbaryl, methomyl, promacyl and propoxur may be mentioned here as being particularly preferred for use against ectoparasites; or organophosphates, for example acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion; azamethiphos, chlorfenvinphos, chlorpyrifos, coumaphos, cythioate, diazinon (dimpylate), dichlorvos (DDVP), dicrotophos, dimethoate, ethion (diethion), famphur (famophos), fenitrothion, fenthion (MPP), heptenophos, malathion, naled, phosmet (PMP, phtalofos), phoxim, propetamphos, temephos, tetrachlorvinphos (CVMP) and triclorfon/metrifonate may be mentioned here as being particularly preferred for use against ectoparasites.

(I-2) GABA-gated chloride channel antagonists, such as, for example, organochlorines, for example, bromocyclene, chlordane and endosulfan (alpha-), heptachlor, lindane, and toxaphene; endosulphan (alpha-) and lindane may be mentioned here as being particularly preferred for use against ectoparasites; or fiproles (phenylpyrazoles), for example acetoprole, ethiprole, fipronil, pyrafluprole and pyriprole, rizazole; fipronil and pyriprole may be mentioned here as being particularly preferred for use against ectoparasites; or arylisoxazolines, arylpyrrolines, arylpyrrolidines, for example, A1443 (known from WO2009/2024541, Ex. 11-1; but also compounds from WO 2007/075459, WO 2007/125984, WO 2005/085216, WO 2009/002809), and structurally related arylpyrrolines (known from WO2009/072621, WO 2010020522, WO 2009112275, WO 2009097992, WO 2009072621, JP 2008133273, JP 2007091708), or arylpyrrolidines (WO 2010090344, WO 2010043315, WO 2008128711, JP 2008110971), A1443 (=Example 11-1 from WO 2009/204541), and also Examples 1 to 4 from US 2010/0173948 may be mentioned here as being particularly preferred for use against ectoparasites.

(I-3) Sodium channel modulators/voltage-dependent sodium channel blockers, such as, for example, pyrethroids, for example acrinathrin, allethrin (d-cis-trans, d-trans), bifenthrin, bioallethrin, bioallethrin-S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers], esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans-isomer], prallethrin, profluthrin, pyrethrins (pyrethrum), resmethrin, RU 15525, silafluofen, tefluthrin, tetramethrin [(1R)-isomers], tralomethrin, transfluthrin and ZXI 8901; the type I pyrethroids allethrin, bioallethrin, permethrin, phenothrin, resmethrin, tetramethrin and the type II pyrethroids (alphacyanopyrethroids) alpha-cypermethrin, cyfluthrin (beta-), cyhalothrin (lambda-), cypermethrin (alpha-, zeta-), deltamethrin, fenvalerate, flucythrinate, flumethrin, fluvalinate (tau-), and the ester-free pyrethroids etofenprox and silafluofen may be mentioned here as being particularly preferred for use against ectoparasites; or organochlorine compounds, for example, DDT; or methoxychlor.

(I-4) Nicotinergic acetylcholine receptor agonists, such as, for example, nicotine or neonicotinoids, for example acetamiprid, clothianidin, dinotefuran, imidacloprid, imidaclothiz, nitenpyram, thiacloprid, thiamethoxam; chlothianidin, dinotefuran, imidacloprid, nitenpyram, and thiacloprid may be mentioned here as being particularly preferred for use against ectoparasites.

(I-5) Allosteric acetylcholine receptor modulators (agonists), such as, for example, spinosyns, for example spinetoram and spinosad; spinosad and spinetoram may be mentioned here as being particularly preferred for use against ectoparasites.

(I-6) Chloride channel activators, such as, for example, avermectins/milbemycins, for example abamectin, doramectin, emamectin benzoate, eprinomectin, ivermectin, latidectin, lepimectin, milbemycin oxime, milbemectin, moxidectin and selamectin; doramectin, eprinomectin, ivermectin, milbemycin oxime, moxidectin and selamectin may be mentioned here as being particularly preferred for use against ectoparasites.

(I-7) Juvenile hormone analogues, for example hydroprene (S—), kinoprene, methoprene (S—); or fenoxycarb; pyriproxyfen; methoprene (S—) and pyriproxyfen may be mentioned here as being particularly preferred for use against ectoparasites.

(I-8) Mite growth inhibitors, for example clofentezine, diflovidazin, hexythiazox, etoxazole; etoxazole may be mentioned here as being particularly preferred for use against ectoparasites.

(I-9) Slo-1 and latrophilin receptor agonists, such as, for example, cyclic depsipeptides, for example, emodepside and its starting material PF1022A (known from EP 382173, compound I); emodepside may be mentioned here as being particularly preferred for use against ectoparasites.

(I-10) Oxidative phosphorylation inhibitors, ATP disruptors, such as, for example, diafenthiuron.

(I-12) Nicotinergic acetylcholine receptor antagonists, such as, for example, bensultap, cartap (hydrochloride), thiocylam, and thiosultap (-sodium).

(I-13) Chitin biosynthesis inhibitors, type 0, such as, for example, benzoylureas, for example bistrifluron, chlorfluazuron, diflubenzuron, flucycloxuron, flufenoxuron, hexaflumuron, lufenuron, novaluron, noviflumuron, teflubenzuron and triflumuron; diflubenzuron, fluazuron, lufenuron and triflumuron may be mentioned here as being particularly preferred for use against ectoparasites.

(I-14) Chitin biosynthesis inhibitors, type 1, such as, for example, buprofezin.

(I-15) Moulting disruptors, such as, for example, cyromazine and dicyclanil; cyromazine and dicyclanil may be mentioned here as being particularly preferred for use against ectoparasites.

(I-16) Ecdysone agonists/disruptors, such as, for example, diacylhydrazines, for example chromafenozide, halofenozide, methoxyfenozide and tebufenozide.

(I-17) Octopaminergic agonists, such as, for example, amitraz, cymiazole and demiditraz; amitraz, cymiazole and demiditraz may be mentioned here as being particularly preferred for use against ectoparasites.

(I-18) Complex-III electron transport inhibitors, such as, for example, hydramethylnon; acequinocyl; fluacrypyrim.

(I-19) Complex-I electron transport inhibitors, for example from the group of the METI acaricides, for example fenazaquin, fenpyroximate, pyrimidifen, pyridaben, tebufenpyrad, tolfenpyrad; fenpyroximate, pyrimidifen and tolfenpyrad may be mentioned here as being particularly preferred for use against ectoparasites;

(I-20) Voltage-dependent sodium channel blockers, such as, for example indoxacarb and metaflumizone; indoxacarb and metaflumizone may be mentioned here as being particularly preferred for use against ectoparasites.

(I-21) Inhibitors of acetyl-CoA carboxylase, such as, for example, tetronic acid derivatives, for example spirodiclofen and spiromesifen; or tetramic acid derivatives, for example spirotetramat.

(I-22) Complex-II electron transport inhibitors, such as, for example, cyenopyrafen.

(I-23) Ryanodine receptor effectors, such as, for example, diamides, for example flubendiamide, chlorantraniliprole (Rynaxypyr), cyantraniliprole (Cyazypyr) and also 3-bromo-N-{2-bromo-4-chloro-6-[(1-cyclopropylethyl)carbamoyl] phenyl}-1-(3-chloropyridin-2-yl)-1H-pyrazole-5-carboxamide (known from WO2005/077934) or methyl 2-[3,5-dibromo-2-({[3-bromo-1-(3-chloropyridin-2-yl)-1H-pyrazol-5-yl]carbonyl}amino)benzoyl]-1,2-dimethylhydrazinecarboxylate (known from WO2007/043677).

(I-24) Further active compounds with unknown mechanism of action, such as, for example, azadirachtin, amidoflumet, benzoximate, bifenazate, chinomethionat, cryolite, cyflumetofen, dicofol, fluensulfone (5-chloro-2-[(3,4,4-trifluorobut-3-en-1-yl)sulphonyl]-1,3-thiazole), flufenerim, pyridalyl and pyrifluquinazon; and also products based on *Bacillus firmus* (I-1582, BioNeem, Votivo) and also the known active compounds below 4-{[(6-bromopyrid-3-yl) methyl](2-fluoroethyl)amino}furan-2(5H)-one (known from WO 2007/115644), 4-{[(6-fluoropyrid-3-yl)methyl](2,2-difluoroethyl)amino}furan-2(5H)-one (known from WO 2007/115644), 4-{[(2-chloro-1,3-thiazol-5-yl)methyl](2-fluoroethyl)amino}furan-2(5H)-one (known from WO 2007/115644), 4-{[(6-chloropyrid-3-yl)methyl](2-fluoroethyl) amino}furan-2(5H)-one (known from WO 2007/115644), 4-{[(6-chloropyrid-3-yl)methyl](2,2-difluoroethyl) amino}furan-2(5H)-one (known from WO 2007/115644), 4-{[(6-chloro-5-fluoropyrid-3-yl)methyl](methyl) amino}furan-2(5H)-one (known from WO 2007/115643), 4-{[(5,6-dichloropyrid-3-yl)methyl](2-fluoroethyl) amino}furan-2(5H)-one (known from WO 2007/115646), 4-{[(6-chloro-5-fluoropyrid-3-yl)methyl](cyclopropyl) amino}furan-2(5H)-one (known from WO 2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), [(6-chloropyridin-3-yl)methyl](methyl)oxido-λ⁴-sulphanylidenecyanamide (known from WO 2007/149134), [1-(6-chloropyridin-3-yl)ethyl](methyl) oxido-λ⁴-sulphanylidenecyanamide (known from WO 2007/149134) and its diastereomers (A) and (B)

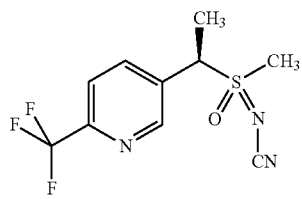

(A)

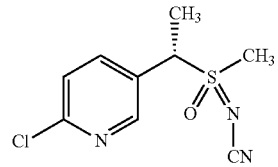

(B)

(also known from WO 2007/149134), [(6-trifluoromethylpyridin-3-yl)methyl](methyl)oxido-λ⁴-sulphanylidenecyanamide (known from WO 2007/095229), sulfoxaflor (also known from WO 2007/149134), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), 1-[2-fluoro-4-methyl-5-[(2,2,2-trifluoroethyl) sulphinyl]phenyl]-3-(trifluoromethyl)-1H-1,2,4-triazole-5-amine (known from WO 2006/043635), [(3S,4aR,12R,12aS,12bS)-3-[(cyclopropylcarbonyl)oxy]-6,12-dihydroxy-4,12b-di-methyl-11-oxo-9-(pyridin-3-yl)-1,3,4,4a,5,6,6a,12,12a,12b-decahydro-2H,11H-benzo[f]pyrano[4,3-b]-chromen-4-yl]methyl cyclopropanecarboxylate (known from WO 2006/129714), 2-cyano-3-(difluoro-methoxy)-N-ethylbenzenesulphonamide (known from WO 2005/035486), N-[1-(2,3-dimethylphenyl)-2-(3,5-dimethylphenyl)ethyl]-4,5-dihydro-2-thiazolamine (known from WO 2008/104503); penigequinolone A (known from EP 2248422 (compound I) and WO 2009/060015 (compound No. 11).

(I-25) MGK264 (N-octylbicycloheptenecarboxamide), piperonyl butoxide (PBO) and verbutin may be mentioned here as suitable synergists for use with ectoparasiticides; piperonyl butoxide and MGK264 may be mentioned as being particularly preferred.

From groups (I-1) to (I-25) mentioned above, the following groups are preferred as component B: (I-2), (I-3), (I-4), (I-5), (I-6), (I-17), (I-25).

According to a further embodiment, the following groups are preferred as component B: (I-2), (I-3), (I-4), (I-5), (I-6), (I-17).

Preferred examples of insecticidally or acaricidally active compounds or synergists of component B are endosulphan (alpha-), lindane; fipronil, pyriprole; A1443 (Example 11-1 from WO 2009/2024541); allethrin, bioallethrin, permethrin, phenothrin, resmethrin, tetramethrin; cyfluthrin (beta-), cyhalothrin (lambda-), cypermethrin (alpha-, zeta-), deltamethrin, fenvalerate, flucythrinate, flumethrin, fluvalinate (tau-); etofenprox, silafluofen; chlothianidin, dinotefuran, imidacloprid, nitenpyram, thiacloprid; spinosad, spinetoram; doramectin, eprinomectin, ivermectin, milbemycin oxime, moxidectin, selamectin; amitraz, cymiazole, demiditraz; piperonyl butoxide, MGK264.

Preference is given to active compound combinations (Nos. 1 to 39) in which one active compound of component A is combined with the active compounds below of component B, in the mixing ratios given in Table A. These active compound combinations are listed in Table 3 below. The mixing ratios in the table are based on weight ratios. The ratio is to be understood as meaning component A:component B.

TABLE 3

| Grp. | No. B- | Component B (=mixing partner of component A) | preferred mixing ratio | particularly preferred mixing ratio | very particularly preferred mixing ratio |
|---|---|---|---|---|---|
| I-2 | 1 | Ex. 11-1 from WO 2009/2024541 | 125:1 to 1:125 | 25:1 to 1:25 | 5:1 to 1:5 |
| I-3 | 2 | allethrin | 125:1 to 1:125 | 25:1 to 1:25 | 5:1 to 1:5 |
| I-17 | 3 | amitraz | 125:1 to 1:125 | 25:1 to 1:25 | 5:1 to 1:5 |
| I-3 | 4 | bioallethrin | 125:1 to 1:125 | 25:1 to 1:25 | 5:1 to 1:5 |
| I-4 | 5 | chlothianidin | 125:1 to 1:125 | 25:1 to 1:25 | 5:1 to 1:5 |
| I-3 | 6 | cyfluthrin (beta-) | 125:1 to 1:125 | 25:1 to 1:25 | 5:1 to 1:5 |
| I-3 | 7 | cyhalothrin (lambda-) | 125:1 to 1:125 | 25:1 to 1:25 | 5:1 to 1:5 |
| I-17 | 8 | cymiazole | 125:1 to 1:125 | 25:1 to 1:25 | 5:1 to 1:5 |
| I-3 | 9 | cypermethrin (alpha-, zeta-) | 125:1 to 1:125 | 25:1 to 1:25 | 5:1 to 1:5 |
| I-3 | 10 | deltamethrin | 125:1 to 1:125 | 25:1 to 1:25 | 5:1 to 1:5 |
| I-17 | 11 | demiditraz | 125:1 to 1:125 | 25:1 to 1:25 | 5:1 to 1:5 |
| I-4 | 12 | dinotefuran | 125:1 to 1:125 | 25:1 to 1:25 | 5:1 to 1:5 |
| I-6 | 13 | doramectin | 125:1 to 1:125 | 25:1 to 1:25 | 5:1 to 1:5 |
| I-2 | 14 | endosulphan (alpha-) | 125:1 to 1:125 | 25:1 to 1:25 | 5:1 to 1:5 |
| I-6 | 15 | eprinomectin | 125:1 to 1:125 | 25:1 to 1:25 | 5:1 to 1:5 |
| I-3 | 16 | etofenprox | 125:1 to 1:125 | 25:1 to 1:25 | 5:1 to 1:5 |
| I-3 | 17 | fenvalerate | 125:1 to 1:125 | 25:1 to 1:25 | 5:1 to 1:5 |
| I-2 | 18 | fipronil | 125:1 to 1:125 | 25:1 to 1:25 | 5:1 to 1:5 |
| I-3 | 19 | flucythrinate | 125:1 to 1:125 | 25:1 to 1:25 | 5:1 to 1:5 |
| I-3 | 20 | flumethrin | 125:1 to 1:125 | 25:1 to 1:25 | 5:1 to 1:5 |
| I-3 | 21 | fluvalinate (tau-) | 125:1 to 1:125 | 25:1 to 1:25 | 5:1 to 1:5 |
| I-4 | 22 | imidacloprid | 125:1 to 1:125 | 25:1 to 1:25 | 5:1 to 1:5 |
| I-6 | 23 | ivermectin | 125:1 to 1:125 | 25:1 to 1:25 | 5:1 to 1:5 |
| I-2 | 24 | lindane | 125:1 to 1:125 | 25:1 to 1:25 | 5:1 to 1:5 |
| I-25 | 25 | MGK264 | 125:1 to 1:125 | 25:1 to 1:25 | 5:1 to 1:5 |
| I-6 | 26 | milbemycin oxime | 125:1 to 1:125 | 25:1 to 1:25 | 5:1 to 1:5 |
| I-6 | 27 | moxidectin | 125:1 to 1:125 | 25:1 to 1:25 | 5:1 to 1:5 |
| I-4 | 28 | nitenpyram | 125:1 to 1:125 | 25:1 to 1:25 | 5:1 to 1:5 |
| I-3 | 29 | permethrin | 125:1 to 1:125 | 25:1 to 1:25 | 5:1 to 1:5 |
| I-3 | 30 | phenothrin | 125:1 to 1:125 | 25:1 to 1:25 | 5:1 to 1:5 |
| I-25 | 31 | piperonyl butoxide | 125:1 to 1:125 | 25:1 to 1:25 | 5:1 to 1:5 |
| I-2 | 32 | pyriprole | 125:1 to 1:125 | 25:1 to 1:25 | 5:1 to 1:5 |
| I-3 | 33 | resmethrin | 125:1 to 1:125 | 25:1 to 1:25 | 5:1 to 1:5 |
| I-6 | 34 | selamectin | 125:1 to 1:125 | 25:1 to 1:25 | 5:1 to 1:5 |
| I-3 | 35 | silafluofen | 125:1 to 1:125 | 25:1 to 1:25 | 5:1 to 1:5 |
| I-5 | 36 | spinetoram | 125:1 to 1:125 | 25:1 to 1:25 | 5:1 to 1:5 |
| I-5 | 37 | spinosad | 125:1 to 1:125 | 25:1 to 1:25 | 5:1 to 1:5 |
| I-3 | 38 | tetramethrin | 125:1 to 1:125 | 25:1 to 1:25 | 5:1 to 1:5 |
| I-4 | 39 | thiacloprid | 125:1 to 1:125 | 25:1 to 1:25 | 5:1 to 1:5 |

The active compounds of group I-17 have no practically relevant activity towards insects. With regard to the control of insects, according to one embodiment of the present invention, the active compounds of group I-17 are therefore excluded as component B from the embodiments mentioned above—including preferred and particularly preferred embodiments.

The active compound combinations according to the invention are highly suitable for controlling animal pests in the field of veterinary medicine.

If, in the context of this description, the short form of the common name of an active compound is used, this comprises in each case all customary derivatives, such as the esters and salts, and isomers, in particular optical isomers, especially the commercially available form or forms. If the common name refers to an ester or a salt, this in each case also comprises all other customary derivatives, such as other esters and salts, the free acids and neutral compounds, and isomers, in particular optical isomers, especially the commercially available form or forms. The given chemical compound names refer to at least one of the compounds embraced by the common name, frequently to a preferred compound.

Surprisingly, the insecticidal and/or acaricidal activity of the active compound combinations according to the invention is improved compared to the sum of the activities of the individual active compounds in components A and B. A widened activity spectrum and/or an improved activity are desirable; preferably, an unforeseeable true synergistic effect is present.

The active compound combinations according to the invention, in combination with favourable toxicity to warm-blooded animals and being tolerated well by the environment, are suitable for use in the animal health field, i.e. in the field of veterinary medicine. Here, the active compound combinations according to the present invention are active against animal parasites, in particular ectoparasites. Ectoparasites are typically and preferably arthropods, in particular insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like.

These parasites include from the order of the Anoplurida, for example *Haematopinus* spp., *Linognathus* spp., *Pediculus* spp., *Phtirus* spp., *Solenopotes* spp.; particular examples are: *Linognathus setosus*, *Linognathus vituli*, *Linognathus ovillus*, *Linognathus oviformis*, *Linognathus pedalis*, *Linognathus stenopsis*, *Haematopinus asini macrocephalus*, *Haematopinus eurysternus*, *Haematopinus suis*, *Pediculus humanus capitis*, *Pediculus humanus corporis*, *Phylloera vastatrix*, *Phthirus pubis*, *Solenopotes capillatus*;

from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; particular examples are: *Bovicola bovis*, *Bovicola ovis*, *Bovicola limbata*, *Damalina bovis*, *Trichodectes canis*, *Felicola subrostratus*, *Bovicola caprae*, *Lepikentron ovis*, *Werneckiella equi*;

from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particular examples are: *Aedes aegypti*, *Aedes albopictus*, *Aedes taeniorhynchus*, *Anopheles gambiae*, *Anopheles maculipennis*, *Calliphora erythrocephala*, *Chrysozona pluvialis*, *Culex quinquefasciatus*, *Culex pipiens*, *Culex tarsalis*, *Fannia canicularis*, *Sarcophaga carnaria*, *Stomoxys calcitrans*, *Tipula paludosa*, *Lucilia cuprina*, *Lucilia sericata*, *Simulium reptans*, *Phlebotomus papatasi*, *Phlebotomus longipalpis*, *Odagmia ornata*, *Wilhelmia equina*, *Boophthora erythrocephala*, *Tabanus bromius*, *Tabanus spodopterus*, *Tabanus atratus*, *Tabanus sudeticus*, *Hybomitra ciurea*, *Chrysops caecutiens*, *Chrysops relictus*, *Haematopota pluvialis*, *Haematopota italica*, *Musca autumnalis*, *Musca domestica*, *Haematobia irritans irritans*, *Haematobia irritans exigua*, *Haematobia stimulans*, *Hydrotaea irritans*, *Hydrotaea albipuncta*, *Chrysomya chloropyga*, *Chrysomya bezziana*, *Oestrus ovis*, *Hypoderma bovis*, *Hypoderma lineatum*, *Przhevalskiana silenus*, *Dermatobia hominis*, *Melophagus ovinus*, *Lipoptena capreoli*, *Lipoptena cervi*, *Hippobosca variegata*, *Hippobosca equina*, *Gasterophilus intestinalis*, *Gasterophilus*

*haemorrhoidalis, Gasterophilus inermis, Gasterophilus nasalis, Gasterophilus nigricornis, Gasterophilus pecorum, Braula coeca;* from the order of the Siphonapterida, for example *Pulex* spp., *Ctenocephalides* spp., *Tunga* spp., *Xenopsylla* spp., *Ceratophyllus* spp.; particular examples are: *Ctenocephalides canis, Ctenocephalides felis, Pulex irritans, Tunga penetrans, Xenopsylla cheopis;* from the order of the Heteropterida, for example *Cimex* spp., *Triatoma* spp., *Rhodnius* spp., *Panstrongylus* spp.

from the subclass of the Acari (Acarina) and the orders of the Meta- and Mesostigmata, for example *Argas* spp., *Ornithodorus* spp., *Otobius* spp., *Ixodes* spp., *Amblyomma* spp., *Rhipicephalus (Boophilus)* spp., *Dermacentor* spp., *Haemophysalis* spp., *Hyalomma* spp., *Dermanyssus* spp., *Rhipicephalus* spp. (the original genus of multi-host ticks) *Ornithonyssus* spp., *Pneumonyssus* spp., *Raillietia* spp., *Pneumonyssus* spp., *Sternostoma* spp., *Varroa* spp., *Acarapis* spp.; particular examples are: *Argas persicus, Argas reflexus, Ornithodorus moubata, Otobius megnini, Rhipicephalus (Boophilus) microplus, Rhipicephalus (Boophilus) decoloratus, Rhipicephalus (Boophilus) annulatus, Rhipicephalus (Boophilus) calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni;* from the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particular examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae (=S. caprae), Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.*

The active compound combinations according to the invention are also suitable for controlling arthropods which attack animals. Animals include agricultural livestock such as, for example, cattle, sheep, goats, horses, pigs, donkeys, camels, buffaloes, rabbits, chickens, turkeys, ducks, geese, cultured fish, honeybees. Moreover, animals include domestic animals—also referred to as companion animals—such as, for example, dogs, cats, cage birds, aquarium fish and what are known as experimental animals such as, for example, hamsters, guinea pigs, rats and mice.

By controlling these arthropods, it is intended to reduce deaths and improve performance (in the case of meat, milk, wool, hides, eggs, honey and the like) and health of the host animal, so that more economical and simpler animal keeping is made possible by the use of the active compounds according to the invention.

For example, it is desirable to prevent or interrupt the uptake of blood by the parasites from the host (when applicable). Also, controlling the parasites may help to prevent the transmittance of infectious agents.

The term "controlling" as used herein with regard to the animal health field, means that the active compounds are effective in reducing the incidence of the respective parasite in an animal infected with such parasites to innocuous levels. More specifically, "controlling", as used herein, means that the active compound is effective in killing the respective parasite, inhibiting its growth, or inhibiting its proliferation.

Generally, when used for the treatment of animals, the active compounds according to the invention can be applied directly. Preferably they are applied as pharmaceutical compositions which may contain pharmaceutically acceptable excipients and/or auxiliaries which are known in the art.

In the animal health field and in animal keeping, the active compounds are applied (=administered) in the known manner by enteral administration in the form of, for example, tablets, capsules, drinks, drenches, granules, pastes, boluses, the feed-through method, suppositories; by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like. The active compounds may be formulated as shampoo or as suitable formulations usable in aerosols or unpressurized sprays, for example pump sprays and atomizer sprays.

When used for livestock, poultry, domestic animals and the like, the active compounds according to the invention can be applied as formulations (for example powders, wettable powders ["WP"], emulsions, emulsifiable concentrates ["EC"], flowables, homogeneous solutions, and suspension concentrates ["SC"]) which comprise the active compounds in an amount of from 1 to 80% by weight, either directly or after dilution (e.g. 100- to 10 000-fold dilution), or else as a chemical bath.

Naturally, the general broad activity spectrum of the mixtures in the arthropod field also allows control of hygiene pests, which are listed below:

From the order of the Heteroptera, for example *Anasa tristis, Antestiopsis* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., Pentomidae, *Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

From the order of the Homoptera, for example *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp.,

*Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of the Hymenoptera, for example *Athalia* spp., *Diprion* spp., *Hoplocampa* spp., *Lasius* spp., *Monomorium pharaonis, Vespa* spp.

From the order of the Isopoda, for example *Armadillidium vulgare, Oniscus asellus, Porcellio scaber.*

From the order of the Isoptera, for example *Acromyrmex* spp., *Atta* spp., *Cornitermes cumulans, Microtermes obesi, Odontotermes* spp., *Reticulitermes* spp, From the order of the Lepidoptera, for example Acronicta major, *Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia kuehniella, Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllono-* *rycter* spp., *Pieris* spp., *Platynota stultana, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichoplusia* spp., *Tuta absoluta, Virachola* spp.

From the order of the Orthoptera, for example *Acheta domesticus, Blatta orientalis, Blattella germanica, Dichroplus* spp., *Gryllotalpa* spp., *Leucophaea maderae, Locusta* spp., *Melanoplus* spp., *Supella* spp., *Periplaneta americana, Schistocerca gregaria.*

From the order of the Symphyla, for example *Scutigerella* spp.

From the order of the Thysanura, for example *Lepisma saccharina.*

"Combination" or the use in combination means that the components A and B are formulated in a joint preparation and are accordingly applied together. However, the products may also comprise separate preparations for each active compound. Accordingly, if more than two active compounds are to be applied, all active compounds may be formulated in a joint preparation or all active compounds may be formulated in separate formulations; also feasible are mixed forms where some of the active compounds are formulated jointly and some of the active compounds are formulated separately.

Separate formulations allow the separate or successive application of the active compounds in question.

EXAMPLES

Preparation Example A-15

Step 1:
[3,5-Dichloro-4-(dimethylamino)phenyl]acetonitrile

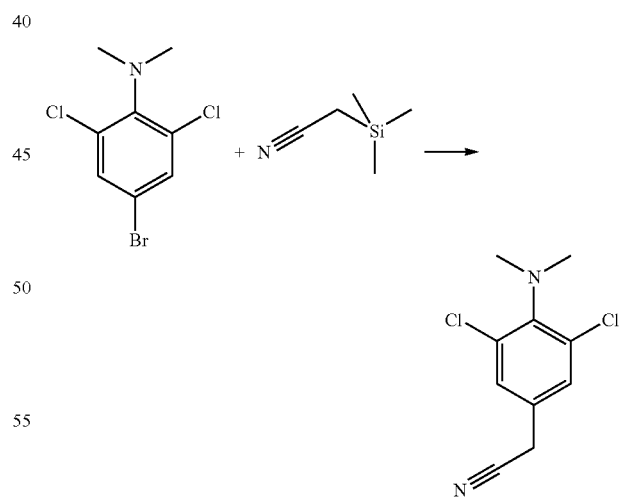

In a glass tube with screw-on lid, 2 g (7.43 mmol) of 4-bromo-2,6-dichloro-N,N-dimethylaniline (known from European Journal of Organic Chemistry (2006), (19), 4398-4404) are initially charged with 86 mg (0.14 mmol) of xantphos and 136 mg (0.14 mmol) of tris(dibenzylideneacetone)-dipalladium in 10 ml of DMF. 1.01 g (8.92 mmol) of trimethylsilylacetonitrile and 0.46 g (4.46 mmol) of zinc fluoride are then added, and in the closed vessel the reaction is heated at 90° C. for 16 hours. The reaction mixture is cooled, water and ethyl acetate are added and the mixture is filtered through silica gel.

The organic phase is separated off, dried over magnesium sulphate and concentrated. The crude product is chromatographed on a silica gel cartridge using a cyclohexane/ethyl acetate gradient. This gives 0.9 g (52.8% of theory) of the title compound as a colourless oil.

$^1$H-NMR: (400 MHz, DMSO-d6), δ 7.42 (s, 2H), 4.01 (s, 2H), 2.81 (s, 6H).

Step 2: 2-[3,5-Dichloro-4-(dimethylamino)phenyl]-4,4,4-trifluoro-3-oxobutanenitrile

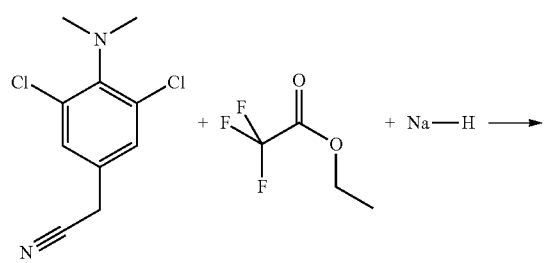

1.41 g (35.3 mmol) of sodium hydride are initially charged in absolute THF (50 ml), and 4.05 g (17.6 mmol) of [3,5-dichloro-4-(dimethylamino)phenyl]acetonitrile in 20 ml of absolute THF are added dropwise at 0° C. The mixture is stirred at 0° C. for 20 minutes, and 5.02 g (35.3 mmol) of ethyl trifluoroacetate are then added dropwise at 0° C. The reaction mixture is warmed to room temperature and then carefully added to water. After washing with n-hexane, the aqueous phase is acidified with 1 N HCl. A colourless solid precipitates out and is, after filtration with suction and air-drying, used without further purification for the next step.

Step 3: (2E)-3-Chloro-2-[3,5-dichloro-4-(dimethylamino)phenyl]-4,4,4-trifluorobut-2-enenitrile)

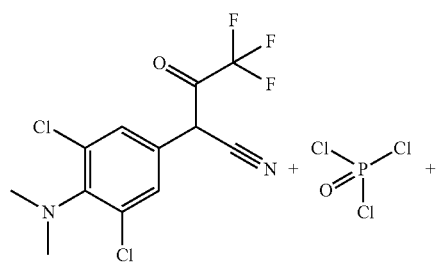

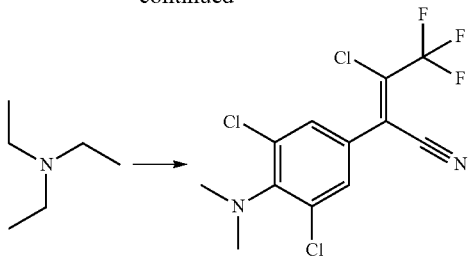

1 g (3.07 mmol) of 2-[3,5-dichloro-4-(dimethylamino)phenyl]-4,4,4-trifluoro-3-oxobutanenitrile is initially charged in 1.44 ml of POCl$_3$ (15.3 mmol), and 0.43 ml (3.07 mmol) of triethylamine are added slowly. The reaction mixture is then stirred under reflux for 5 hours. After cooling, water is added carefully and the mixture is extracted repeatedly with dichloromethane. The separated organic phases are combined, dried over magnesium sulphate, filtered and concentrated. The residue is used without further purification for the next step.

Step 4: (A-15)

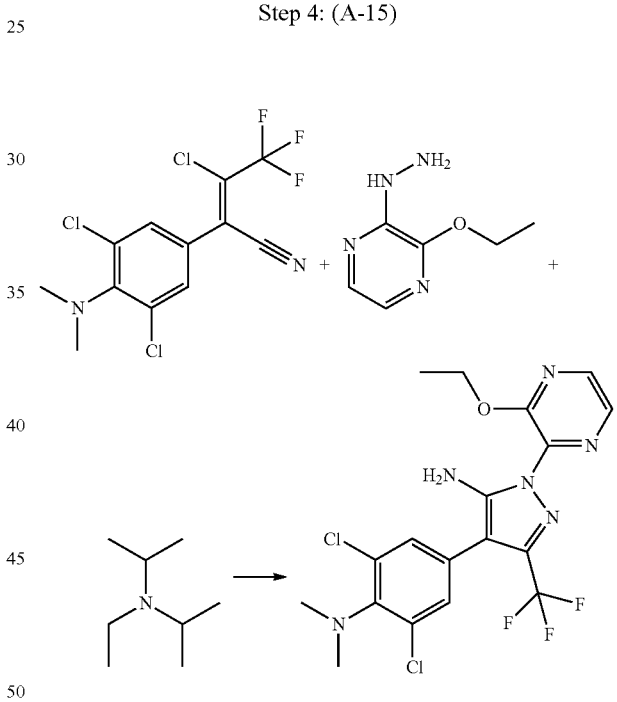

0.5 g (1.45 mmol) of (2E)-3-chloro-2-[3,5-dichloro-4-(dimethylamino)phenyl]-4,4,4-trifluorobut-2-enenitrile, 0.224 g (1.45 mmol) of 2-ethoxy-3-hydrazinopyrazine and 0.376 g (2.91 mmol) of N-ethyldiisopropylamine in 25 ml of THF are stirred under reflux for 6 hours. After cooling, the solvent is distilled off under reduced pressure, 30 ml of water are added to the residue and the mixture is extracted repeatedly with dichloromethane. The separated organic phases are combined, dried over magnesium sulphate, filtered and concentrated. The residue is stirred with n-pentane and the precipitate formed is filtered off with suction and air-dried. This gives 0.548 g (75.9% of theory) of the title compound as a colourless solid.

1H NMR (400 MHz, DMSO-d6), δ 8.44 (d, 1H), 8.25 (d, 1H), 7.33 (s, 2H), 5.97 (bs, 2H, NH$_2$), 4.47 (q, 2H), 2.86 (s, 6H), 1.32 (t, 3H).

USE EXAMPLES

According to S. R. Colby, Weeds 15 (1967), 20-22, the expected action for a given combination of two active compounds can be calculated as follows: if X is the kill rate, expressed in % of the untreated control, when employing active compound A at an application rate of m g/ha or in a concentration of m ppm, Y is the kill rate, expressed in % of the untreated control, when employing active compound B at an application rate of n g/ha or in a concentration of n ppm and E is the kill rate, expressed in % of the untreated control, when employing active compounds A and B at application rates of m and n g/ha or in a concentration of m and n ppm, then $$E = X + Y - \frac{X \cdot Y}{100}$$

If the actual kill rate exceeds the calculated value, the killing action of the combination is superadditive, i.e. a synergistic effect is present. In this case, the actually observed kill rate must exceed the value calculated using the above formula for the expected kill rate (E).

In vitro contact tests with ticks and fleas

From Table 1, representatives of important classes of active compounds (component B) were now tested in combination with pyrazine derivatives of the formula (I) according to the invention as component A against arachnids and insects. To this end, roll-necked test tubes were coated with a solution of active compound A or B or a combination of the two in acetone (2 h of swing rotation at 30 rpm in a fume cupboard). After evaporation of the solvent, the test tubes were populated with 10-20 adult fleas (*Ctenocephalides felis*) or with 5-10 ticks (adult *Rhipicephalus sanguineus*) and closed with a perforated plastic lid. After 24 h and after 48 h, the activity was determined and the potential synergistic effect of the active compound combination was evaluated using the formula described above.

For Example A1

For Example B-1 from Table 3, mixtures of A-1:B-1 of from 1:5 to 1:25 showed synergistic effects on the mortality of cat fleas (*Ctenocephalides felis*) at 7.2 µg/dm² of component B-1 after 48 h.

Against brown dog ticks (*Rhipicephalus sanguineus*), mixtures of A-1:B-1 in a ratio of from 1:1 to 1:25 were synergistically active at 1.4 µg/dm² of component B-1 after 24 and 48 h.

For Example B-11 from Table 3, as expected, no insecticidal activity was observed in the contact test method, since the active compound class of these amidines shows virtually no relevant insecticidal activity in veterinary indications. Accordingly, under the test conditions, the insecticidal activity of component A-1 in combinations with B-11 was unchanged.

In the case of mixtures with component A-1, mixtures of A-1:B-11 of from 125:1 to 1:25 showed strong synergistic effects on the mortality of brown dog ticks (*Rhipicephalus sanguineus*) at 0.288-7.2 µg/dm² of component A-1 after 24 h and 48 h.

For Example B-18 from Table 3, mixtures with component A-1 of A-1:B-18 of from 1:25 to 25:1 showed synergistic effects on the mortality of cat fleas (*Ctenocephalides felis*) at 0.06-1.4 µg/dm² of component A-1 after 48 h.

For Example B-18 from Table 3, mixtures with component A-1 of A-1:B-18 of from 1:25 to 25:1 showed synergistic effects on the mortality of brown dog ticks (*Rhipicephalus sanguineus*) at 0.06-1.4 µg/dm² of component A-1 after 48 h.

For Example B-20 from Table 3, mixtures with component A-1 of A-1:B-20 of from 1:25 to 5:1 showed synergistic effects on the mortality of cat fleas (*Ctenocephalides felis*) at 0.06-1.4 µg/dm² of component A-1 after 24 h.

Against brown dog ticks (*Rhipicephalus sanguineus*), mixtures of A-1:B-20 in a ratio of 5:1 and higher (in the present application "higher" means that the ratio seen as a fraction has a greater value, i.e. a ratio of 6:1 is higher than 5:1 and 6:2 is lower than 5:1) had a synergistic effect on the mortality at 1.4 µg/dm² of component A-1 after 48 h.

For Example B-25 from Table 3, mixtures with component A-1 of A-1:B-25 of from 1:125 to 25:1 showed synergistic effects on the mortality of cat fleas (*Ctenocephalides felis*) at 7.2 µg/dm² of component A-1 after 48 h.

Against brown dog ticks (*Rhipicephalus sanguineus*), mixtures of A-1:B-25 in a ratio of 25:1 and higher were synergistically active at 7.2 µg/dm² of component A-1 after 24 h.

For Example B-27 from Table 3, mixtures with component A-1 of A-1:B-27 of from 1:125 to 25:1 showed synergistic effects on the mortality of cat fleas (*Ctenocephalides felis*) at 0.06-7.2 µg/dm² of component A-1 after 24 h.

Against brown dog ticks (*Rhipicephalus sanguineus*), mixtures of A-1:B-27 in a ratio of from 125:1 to 1:125 were synergistically active at 1.4 µg/dm² of component A-1 after 48 h.

For Example B-29 from Table 3, mixtures with component A-1 of A-1:B-29 of from 1:5 to 25:1 showed synergistic effects on the mortality of cat fleas (*Ctenocephalides felis*) at 7.2 µg/dm² of component A-1 after 48 h.

Against brown dog ticks (*Rhipicephalus sanguineus*), mixtures of A-1:B-29 in a ratio of from 1:5 to 5:1 were synergistically active at 1.4 µg/dm² of component A-1 after 48 h.

For Example B-37 from Table 3, mixtures with component A-1 of A-1:B-37 of from 1:125 to 5:1 showed synergistic effects on the mortality of brown dog ticks (*Rhipicephalus sanguineus*) at 1.4 µg/dm² of component A-1 after 48 h.

Against cat fleas (*Ctenocephalides felis*), mixtures of A-1:B-37 in a ratio of 1:5 were synergistically active at 1.4 µg/dm² of component A-1 after 48 h.

For Example A14

For Example B-1 from Table 3, mixtures of A-14:B-1 of from 1:1 to 1:125 showed synergistic effects on the mortality of cat fleas (*Ctenocephalides felis*) at 7.2 µg/dm² of component B-1 after 48 h.

Against brown dog ticks (*Rhipicephalus sanguineus*), mixtures of A-14:B-1 in a ratio of from 1:1 to 1:25 were synergistically active at 7.2 and 1.4 µg/dm² of component B-1 after 24 h.

For Example B-11 from Table 3, as expected, no insecticidal activity was observed in the contact test method, since the active compound class of these amidines shows virtually no relevant insecticidal activity in veterinary indications. Accordingly, under the test conditions, the insecticidal activity of component A-14 in combinations with B-11 was virtually unchanged.

In the case of mixtures with component B-11, mixtures of A-14:B-11 of from 25:1 to 1:125 showed synergistic effects on the mortality of brown dog ticks (*Rhipicephalus sanguineus*) at 0.288-7.2 µg/dm² of component A-14 after 48 h.

For Example B-18 from Table 3, mixtures with component A-14 of A-14:B-18 of from 1:25 to 25:1 showed synergistic effects on the mortality of cat fleas (*Ctenocephalides felis*) at 0.06-1.4 μg/dm² of component A-14 after 48 h.

For Example B-18 from Table 3, mixtures with component A-14 of A-1:B-18 of from 1:25 to 5:1 showed synergistic effects in the activity against brown dog ticks (*Rhipicephalus sanguineus*) at 1.4 μg/dm² of component B-18 after 48 h.

For Example B-20 from Table 3, mixtures with component A-14 of A-14:B-20 of from 1:125 to 5:1 showed synergistic effects on the mortality of cat fleas (*Ctenocephalides felis*) at 0.28-7.2 μg/dm² of component A-14 after 24 h and 48 h.

Against brown dog ticks (*Rhipicephalus sanguineus*), mixtures of A-14:B-20 in a ratio of 5:1 and higher had synergistic effects on the mortality at 1.4-7.2 μg/dm² of component A-14 after 24 h and 48 h.

For Example B-25 from Table 3, mixtures with component A-14 of A-14:B-25 of from 1:125 to 5:1 showed synergistic effects in the activity against cat fleas (*Ctenocephalides felis*) at 7.2-36 μg/dm² of component A-14 after 48 h.

Against brown dog ticks (*Rhipicephalus sanguineus*), mixtures of B-25:A-14 in a ratio of 5:1 and higher were synergistically active at 0.28-1.4 μg/dm² of component A-14 after 24 h.

For Example B-27 from Table 3, mixtures with component A-14 of A-14:B-27 of from 1:125 to 25:1 showed synergistic effects on the mortality of cat fleas (*Ctenocephalides felis*) at 7.2-36 μg/dm² of component A-14 after 24 h.

Against brown dog ticks (*Rhipicephalus sanguineus*), mixtures of A-14:B-27 in a ratio of from 5:1 to 1:125 were synergistically active at 1.4-36 μg/dm² of component A-14 after 48 h.

For Example B-29 from Table 3, mixtures with component A-14 of A-14:B-29 of from 1:5 to 125:1 showed synergistic effects in the activity against cat fleas (*Ctenocephalides felis*) at 1.44-7.2 μg/dm² of component A-14 after 24 h.

Against brown dog ticks (*Rhipicephalus sanguineus*), mixtures of A-14:B-29 in a ratio of from 1:125 to 125:1 were synergistically active at 0.06-1.4 μg/dm² of component A-14 after 48 h.

For Example A15

For Example B-1 from Table 3, mixtures of A-15:B-1 of from 5:1 to 1:125 showed synergistic effects on the mortality of cat fleas (*Ctenocephalides felis*) at 1.4 μg/dm² of component B-1 after 48 h.

Against brown dog ticks (*Rhipicephalus sanguineus*), mixtures of A-15:B-1 in a ratio of 1:5 were synergistically active at 0.288 μg/dm² of component B-1 after 24 and 48 h.

For Example B-11 from Table 3, as expected, no insecticidal activity was observed in the contact test method, since the active compound class of these amidines shows virtually no relevant insecticidal activity in veterinary indications. Accordingly, under the test conditions, the insecticidal activity of component A-15 in combinations with B-11 was unchanged.

In the case of mixtures with component A-15, mixtures of A-15:B-11 of from 125:1 to 1:25 showed synergistic effects on the mortality of brown dog ticks (*Rhipicephalus sanguineus*) at 0.288-7.2 μg/dm² of component A-1 after 48 h.

For Example B-18 from Table 3, mixtures with component A-15 of A-15:B-18 of from 1:25 to 25:1 showed synergistic effects on the mortality of cat fleas (*Ctenocephalides felis*) at 0.28-7.2 μg/dm² of component A-15 after 24 h.

For Example B-18 from Table 3, mixtures with component A-15 showed no changes in activity against brown dog ticks under the test conditions.

For Example B-20 from Table 3, mixtures with component A-15 of A-15:B-20 of 1:25 and higher showed synergistic effects on the mortality of cat fleas (*Ctenocephalides felis*) at 0.06-7.2 μg/dm² of component A-15 after 24 h.

Against brown dog ticks (*Rhipicephalus sanguineus*), mixtures of A-15:B-20 in a ratio of 5:1 and higher acted synergistically on the mortality at 7.2-36 μg/dm² of component A-15 after 48 h.

For Example B-25 from Table 3, mixtures with component A-15 of A-15:B-25 of from 1:125 to 25:1 showed synergistic effects on the mortality of cat fleas (*Ctenocephalides felis*) at 0.28-7.2 μg/dm² of component A-15 after 48 h.

Against brown dog ticks (*Rhipicephalus sanguineus*), mixtures of A-15:B-25 in a ratio of from 1:125 to 5:1 were synergistically active at 1.44-180 μg/dm² of component A-15 after 24 and 48 h.

For Example B-27 from Table 3, mixtures with component A-15 of A-15:B-27 of from 1:25 to 25:1 showed synergistic effects on the mortality of cat fleas (*Ctenocephalides felis*) at 1.44-7.2 μg/dm² of component A-15 after 48 h.

Against brown dog ticks (*Rhipicephalus sanguineus*), mixtures of A-15:B-27 in a ratio of 25:1 to 1:125 showed synergistic effects on the mortality at 0.06-7.2 μg/dm² of component A-1 after 48 h.

For Example B-29 from Table 3, mixtures with component A-15 of A-15:B-29 of from 1:5 to 1:125 showed synergistic effects on the mortality of cat fleas (*Ctenocephalides felis*) at 7.2 μg/dm² of component A-15 after 24 h.

Against brown dog ticks (*Rhipicephalus sanguineus*), mixtures of A-15:B-29 in a ratio of 1:5 to 25:1 showed synergistic effects on the mortality at 0.28-1.4 μg/dm² of component A-15 after 24 h.

For Example B-37 from Table 3, mixtures with component A-15 of A-15:B-37 of from 1:125 to 125:1 showed synergistic effects on the mortality of brown dog ticks (*Rhipicephalus sanguineus*) at 7.2-180 μg/dm² of component A-15 after 48 h.

The invention claimed is:
1. A veterinary pharmaceutical combination comprising, as component A, a compound of the general formula (I)

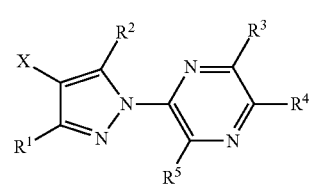

in which

X represents phenyl, 2-pyridyl or 3-pyridyl, each of which is substituted by one or more substituents selected from the group consisting of halogen, alkyl, haloalkyl, alkoxy, alkoxyalkyl, alkoxyalkoxy, cycloalkyl, alkenyloxy, alkynyloxy, benzyloxy, cycloalkylalkoxy, haloalkoxy, haloalkoxyalkyl, alkylsulphanyl, haloalkylsulphanyl, alkylsulphinyl, haloalkylsulphinyl, alkylsulphonyl, haloalkylsulphonyl, cyano, nitro, alkylcarbonyl, alkoxycarbonyl, alkoxycarbonylalkyl, carboxyl, carboxamide, dialkylcarboxamide, trialkylsilyl, amino, alkylamino, dialkyl-amino, alkylsulphonylamino, dialkylsulphonylamino, formyl, —CH=NO—H, —CH=NO-alkyl, —CH=NO-halolkyl, —C(CH₃)=

NO—H, —C(CH₃)=NO-alkyl, —C(CH₃)=NO-haloalkyl; and phenyl, 2-pyridyl and 3-pyridyl which are optionally substituted by one or more halogen atoms, cyano, nitro, alkyl, alkoxy or haloalkyl, where vicinal alkyl, haloalkyl, alkoxy and/or haloalkoxy groups at the phenyl substituent, 2-pyridyl substituent or 3-pyridyl substituent together with the carbon atoms to which they are attached may form a five- to six-membered cyclic system which contains 0 to oxygen or nitrogen atoms, where two oxygen atoms are not directly attached to one another, and whose alkyl moiety may optionally be substituted by one or more halogen atoms and/or further alkyl radicals, $R^1$ represents alkyl which is optionally monosubstituted or independently polysubstituted by alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, hydroxyl and/or cycloalkyl; alkenyl which is optionally monosubstituted or independently polysubstituted by halogen, alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl and/or cycloalkyl; cycloalkyl which is optionally monosubstituted or independently polysubstituted by alkyl, haloalkyl and/or halogen; haloalkyl which is optionally monosubstituted or independently polysubstituted by alkoxy, alkylsulphanyl, haloalkylsulphanyl, alkylsulphinyl, haloalkylsulphinyl, alkylsulphonyl, haloalkylsulphonyl and/or phenyl which is optionally monosubstituted or independently polysubstituted by halogen, alkyl, haloalkyl and/or alkoxy; phenyl which is optionally monosubstituted or independently polysubstituted by halogen, alkyl, haloalkyl and/or alkoxy; benzyl which is optionally monosubstituted or independently polysubstituted by halogen, alkyl, haloalkyl and/or alkoxy; cyano, formyl, alkylcarbonyl, —CH=NO—H, —CH=NO-alkyl, —CH=NO-haloalkyl, —C(CH₃)=NO—H, —C(CH₃)=NO-alkyl or —C(CH₃)=NO-haloalkyl, $R^2$ represents optionally substituted amino, where amino may be monosubstituted or independently disubstituted by alkyl, haloalkyl, alkoxyalkyl, alkylsulphanylalkyl, alkylsulphinylalkyl, alkylsulphonylalkyl, alkylcarbonyl, cycloalkyl, cycloalkylalkyl, alkenyl, where the radicals listed above are optionally substituted by halogen, cyano, alkoxy, alkoxycarbonyl and phenyl, where the phenyl ring is optionally mono- or polysubstituted by one or more substituents independently of one another selected from the group consisting of halogen, alkyl, haloalkyl and alkoxy; alkynyl, alkoxycarbonyl, alkenyloxycarbonyl, alkinyloxycarbonyl, alkoxycarbonylalkyl, alkoxycarbonylcarbonyl, heterocyclyl, heteroaryl, heterocyclylalkyl or heteroarylalkyl, where the heterocyclic or heteroaromatic ring may optionally be mono- or polysubstituted by one or more substituents independently of one another selected from the group consisting of halogen, alkyl, haloalkyl and alkoxy; benzyl or phenylcarbonyl, where the phenyl ring in benzyl and phenylcarbonyl is optionally mono- or polysubstituted by one or more substituents independently of one another selected from the group consisting of halogen, alkyl, haloalkyl and alkoxy, and $R^3$, $R^4$ independently of one another represent hydrogen, halogen, alkyl, cycloalkyl, haloalkyl, cyano, hydroxyl, formyl, alkylcarbonyl, —CH=NO—H, —CH=NO-alkyl, —CH=NO-halo-alkyl, —C(CH₃)=NO—H, —C(CH₃)=NO-alkyl, —C(CH₃)=NO-haloalkyl, nitro, hydroxyl, SH, alkoxy, alkylsulphanyl, haloalkylsulphanyl, alkylsulphinyl, haloalkylsulphinyl, alkylsulphonyl or haloalkylsulphonyl, $R^5$ represents halogen, alkyl, haloalkyl, hydroxyl, alkoxy, alkoxyalkyl, alkoxyalkoxy, cycloalkyl, alkenyloxy, alkynyloxy, benzyloxy, cycloalkylalkoxy, haloalkoxy, haloalkoxyalkyl, —SH, alkyl-sulphanyl, haloalkylsulphanyl, alkylsulphinyl, haloalkylsulphinyl, alkylsulphonyl, haloalkylsulphonyl, cyano, nitro, alkylcarbonyl, alkoxycarbonyl, alkoxycarbonylalkyl, carboxyl, carboxamide, dialkylcarboxamide, trialkylsilyl, amino, alkylamino, dialkylamino, alkylsulphonylamino, dialkylsulphonylamino, formyl, —CH=NO—H, —CH=NO-alkyl, —CH=NO-haloalkyl, —C(CH₃)=NO—H, —C(CH₃)=NO-alkyl, —C(CH₃)=NO-haloalkyl, heteroaryl, where the heteroaromatic ring may optionally be mono- or polysubstituted by one or more substituents independently of one another selected from the group consisting of halogen, alkyl, haloalkyl and alkoxy, or N-oxides or salts thereof, and, as component B, an active compound selected from the group consisting of: (I-1) acetylcholinesterase (AChE) inhibitors; (I-2) GABA-gated chloride channel antagonists; (I-3) sodium channel modulators/voltage-dependent sodium channel blockers; (I-4) nicotinergic acetylcholine receptor agonists; (I-5) allosteric acetylcholine receptor modulators (agonists); (I-6) chloride channel activators; (I-7) juvenile hormone analogues; (I-8) mite growth inhibitors; (I-9) Slo-1 and latrophilin receptor agonists; (I-10) oxidative phosphorylation inhibitors, ATP disruptors; (I-12) nicotinergic acetylcholine receptor antagonists; (I-13) chitin biosynthesis inhibitors, type 0; (I-14) chitin biosynthesis inhibitors, type 1; (I-15) moulting disruptors; (I-16) ecdysone agonists/disruptors; (I-17) octopaminergic agonists; (I-18) complex-III electron transport inhibitors; (I-19) complex-I electron transport inhibitors; (I-20) voltage-dependent sodium channel blockers; (I-21) inhibitors of acetyl-CoA carboxylase; (I-22) complex-II electron transport inhibitors; (I-23) ryanodine receptor effectors; (I-24) active compounds selected from benzoximate, chinomethionat, cyflumetofen, pyridalyl, sulfoxaflor, and penigequinolone A; and (I-25) synergists MGK264 and piperonyl butoxide (PBO).

2. The combination according to claim 1, comprising, as component B, an active compound selected from the group consisting of: (I-2) GABA-gated chloride channel antagonists; (I-3) sodium channel modulators/voltage-dependent sodium channel blockers; (I-4) nicotinergic acetylcholine receptor agonists; (I-5) allosteric acetylcholine receptor modulators (agonists); (I-6) chloride channel activators; (I-17) octopaminergic agonists; and (I-25) synergists MGK264 and piperonyl butoxide (PBO).

3. The combination according to claim 1, comprising, as component A, a compound selected from the group consisting of:

| | |
|---|---|
| A-1 | 4-(7-chloro-1,3-benzodioxol-5-yl)-1-(3-ethoxypyrazin-2-yl)-3-(trifluoromethyl)-1H-pyrazole-5-amine |
| A-2 | 4-(7-chloro-1,3-benzodioxol-5-yl)-1-(3-methoxypyrazin-2-yl)-3-(trifluoromethyl)-1H-pyrazole-5-amine |
| A-3 | 4-(7-chloro-1,3-benzodioxol-5-yl)-1-(3-methoxypyrazin-2-yl)-3-methyl-1H-pyrazole-5-amine |
| A-4 | 4-(7-chloro-1,3-benzodioxol-5-yl)-1-(3-ethoxypyrazin-2-yl)-3-ethyl-1H-pyrazole-5-amine |
| A-5 | 4-(7-chloro-1,3-benzodioxol-5-yl)-1-(3-methoxypyrazin-2-yl)-3-ethyl-1H-pyrazole-5-amine |

-continued

| | |
|---|---|
| A-6 | 4-(7-chloro-1,3-benzodioxol-5-yl)-1-(3-methoxypyrazin-2-yl)-3-isopropyl-1H-pyrazole-5-amine |
| A-7 | 4-(7-chloro-1,3-benzodioxol-5-yl)-1-(3-methoxypyrazin-2-yl)-3-cyclopropyl-1H-pyrazole-5-amine |
| A-8 | 4-(7-bromo-1,3-benzodioxol-5-yl)-1-(3-ethoxypyrazin-2-yl)-3-(trifluoromethyl)-1H-pyrazole-5-amine |
| A-9 | 4-(7-bromo-1,3-benzodioxol-5-yl)-1-(3-methoxypyrazin-2-yl)-3-(trifluoromethyl)-1H-pyrazole-5-amine |
| A-10 | 4-(7-bromo-1,3-benzodioxol-5-yl)-1-(3-ethoxypyrazin-2-yl)-3-ethyl-1H-pyrazole-5-amine |
| A-11 | 4-(7-bromo-1,3-benzodioxol-5-yl)-1-(3-methoxypyrazin-2-yl)-3-ethyl-1H-pyrazole-5-amine |
| A-12 | 1-(3-ethoxypyrazin-2-yl)-3-(trifluoromethyl)-4-[7-(trifluoromethyl)-1,3-benzodioxol-5-yl]-1H-pyrazole-5-amine |
| A-13 | 1-(3-methoxypyrazin-2-yl)-3-(trifluoromethyl)-4-[7-(trifluoromethyl)-1,3-benzodioxol-5-yl]-1H-pyrazole-5-amine |
| A-14 | 4-(3,5-dichloro-4-methoxyphenyl)-1-(3-ethoxypyrazin-2-yl)-3-(trifluoromethyl)-1H-pyrazole-5-amine; and |
| A-15 | 4-[3,5-dichloro-4-(dimethylamino)phenyl]-1-(3-ethoxypyrazin-2-yl)-3-(trifluoromethyl)-1H-pyrazole-5-amine. |

4. The combination according to claim 1, comprising, as component B, a compound selected from the group consisting of: endosulphan (alpha-), lindane; fipronil, pyriprole; A1443; allethrin, bioallethrin, permethrin, phenothrin, resmethrin, tetramethrin; cyfluthrin (beta-), cyhalothrin (lambda-), cypermethrin (alpha-, zeta-), deltamethrin, fenvalerate, flucythrinate, flumethrin, fluvalinate (tau-); etofenprox, silafluofen; chlothianidin, dinotefuran, imidacloprid, nitenpyram, thiacloprid; spinosad, spinetoram; doramectin, eprinomectin, ivermectin, milbemycin oxime, moxidectin, selamectin; amitraz, cymiazole, demiditraz; piperonyl butoxide, and MGK264.

5. The combination according to claim 1, wherein A is 4-(3,5-Dichloro-4-methoxyphenyl)-1-(3-ethoxypyrazin-2-yl)-3-(trifluoromethyl)-1H-pyrazole-5-amine.

6. The combination according to claim 1, wherein A is 4-[3,5-Dichloro-4-(dimethylamino)phenyl]-1-(3-ethoxypyrazin-2-yl)-3-(trifluoromethyl)-1H-pyrazole-5-amine.

7. A method for controlling ectoparasites comprising administering to an animal in need thereof an effective amount of a combination according to claim 1.

8. The method according to claim 7, wherein components A and B of the combination are administered simultaneously.

9. The combination according to claim 1, wherein A is 4-(7-chloro-1,3-benzodioxol-5-yl)-1-(3-ethoxypyrazin-2-yl)-3-(trifluoromethyl)-1H-pyrazole-5-amine, and B is selected from the group consisting of: endosulphan (alpha-), lindane; fipronil, pyriprole; A1443; allethrin, bioallethrin, permethrin, phenothrin, resmethrin, tetramethrin; cyfluthrin (beta-), cyhalothrin (lambda-), cypermethrin (alpha-, zeta-), deltamethrin, fenvalerate, flucythrinate, flumethrin, fluvalinate (tau-); etofenprox, silafluofen; chlothianidin, dinotefuran, imidacloprid, nitenpyram, thiacloprid; spinosad, spinetoram; doramectin, eprinomectin, ivermectin, milbemycin oxime, moxidectin, selamectin; amitraz, cymiazole, demiditraz; piperonyl butoxide, and MGK264.

10. The combination according to claim 1, wherein A is 4-(7-chloro-1,3-benzodioxol-5-yl)-1-(3-methoxypyrazin-2-yl)-3-(trifluoromethyl)-1H-pyrazole-5-amine, and B is selected from the group consisting of: endosulphan (alpha-), lindane; fipronil, pyriprole; A1443; allethrin, bioallethrin, permethrin, phenothrin, resmethrin, tetramethrin; cyfluthrin (beta-), cyhalothrin (lambda-), cypermethrin (alpha-, zeta-), deltamethrin, fenvalerate, flucythrinate, flumethrin, fluvalinate (tau-); etofenprox, silafluofen; chlothianidin, dinotefuran, imidacloprid, nitenpyram, thiacloprid; spinosad, spinetoram; doramectin, eprinomectin, ivermectin, milbemycin oxime, moxidectin, selamectin; amitraz, cymiazole, demiditraz; piperonyl butoxide, and MGK264.

11. The combination according to claim 1, wherein A is 4-(7-chloro-1,3-benzodioxol-5-yl)-1-(3-methoxypyrazin-2-yl)-3-methyl-1H-pyrazole-5-amine, and B is selected from the group consisting of: endosulphan (alpha-), lindane; fipronil, pyriprole; A1443; allethrin, bioallethrin, permethrin, phenothrin, resmethrin, tetramethrin; cyfluthrin (beta-), cyhalothrin (lambda-), cypermethrin (alpha-, zeta-), deltamethrin, fenvalerate, flucythrinate, flumethrin, fluvalinate (tau-); etofenprox, silafluofen; chlothianidin, dinotefuran, imidacloprid, nitenpyram, thiacloprid; spinosad, spinetoram; doramectin, eprinomectin, ivermectin, milbemycin oxime, moxidectin, selamectin; amitraz, cymiazole, demiditraz; piperonyl butoxide, and MGK264.

12. The combination according to claim 1, wherein A is 4-(7-chloro-1,3-benzodioxol-5-yl)-1-(3-ethoxypyrazin-2-yl)-3-ethyl-1H-pyrazole-5-amine, and B is selected from the group consisting of: endosulphan (alpha-), lindane; fipronil, pyriprole; A1443; allethrin, bioallethrin, permethrin, phenothrin, resmethrin, tetramethrin; cyfluthrin (beta-), cyhalothrin (lambda-), cypermethrin (alpha-, zeta-), deltamethrin, fenvalerate, flucythrinate, flumethrin, fluvalinate (tau-); etofenprox, silafluofen; chlothianidin, dinotefuran, imidacloprid, nitenpyram, thiacloprid; spinosad, spinetoram; doramectin, eprinomectin, ivermectin, milbemycin oxime, moxidectin, selamectin; amitraz, cymiazole, demiditraz; piperonyl butoxide, and MGK264.

13. The combination according to claim 1, wherein A is 4-(7-chloro-1,3-benzodioxol-5-yl)-1-(3-methoxypyrazin-2-yl)-3-ethyl-1H-pyrazole-5-amine, and B is selected from the group consisting of: endosulphan (alpha-), lindane; fipronil, pyriprole; A1443; allethrin, bioallethrin, permethrin, phenothrin, resmethrin, tetramethrin; cyfluthrin (beta-), cyhalothrin (lambda-), cypermethrin (alpha-, zeta-), deltamethrin, fenvalerate, flucythrinate, flumethrin, fluvalinate (tau-); etofenprox, silafluofen; chlothianidin, dinotefuran, imidacloprid, nitenpyram, thiacloprid; spinosad, spinetoram; doramectin, eprinomectin, ivermectin, milbemycin oxime, moxidectin, selamectin; amitraz, cymiazole, demiditraz; piperonyl butoxide, and MGK264.

14. The combination according to claim 1, wherein A is 4-(7-chloro-1,3-benzodioxol-5-yl)-1-(3-methoxypyrazin-2-yl)-3-isopropyl-1H-pyrazole-5-amine, and B is selected from the group consisting of: endosulphan (alpha-), lindane; fipronil, pyriprole; A1443; allethrin, bioallethrin, permethrin, phenothrin, resmethrin, tetramethrin; cyfluthrin (beta-), cyhalothrin (lambda-), cypermethrin (alpha-, zeta-), deltamethrin, fenvalerate, flucythrinate, flumethrin, fluvalinate (tau-); etofenprox, silafluofen; chlothianidin, dinotefuran, imidacloprid, nitenpyram, thiacloprid; spinosad, spinetoram; doramectin, eprinomectin, ivermectin, milbemycin oxime, moxidectin, selamectin; amitraz, cymiazole, demiditraz; piperonyl butoxide, and MGK264.

15. The combination according to claim 1, wherein A is 4-(7-chloro-1,3-benzodioxol-5-yl)-1-(3-methoxypyrazin-2-yl)-3-cyclopropyl-1H-pyrazole-5-amine, and B is selected from the group consisting of: endosulphan (alpha-), lindane; fipronil, pyriprole; A1443; allethrin, bioallethrin, permethrin, phenothrin, resmethrin, tetramethrin; cyfluthrin (beta-), cyhalothrin (lambda-), cypermethrin (alpha-, zeta-), deltamethrin, fenvalerate, flucythrinate, flumethrin, fluvalinate (tau-); etofenprox, silafluofen; chlothianidin, dinotefuran, imidacloprid, nitenpyram, thiacloprid; spinosad, spinetoram; doramectin, eprinomectin, ivermectin, milbemycin oxime, moxidectin, selamectin; amitraz, cymiazole, demiditraz; piperonyl butoxide, and MGK264.

16. The combination according to claim 1, wherein A is 4-(7-bromo-1,3-benzodioxol-5-yl)-1-(3-ethoxypyrazin-2-yl)-3-(trifluoromethyl)-1H-pyrazole-5-amine, and B is selected from the group consisting of: endosulphan (alpha-), lindane; fipronil, pyriprole; A1443; allethrin, bioallethrin, permethrin, phenothrin, resmethrin, tetramethrin; cyfluthrin (beta-), cyhalothrin (lambda-), cypermethrin (alpha-, zeta-), deltamethrin, fenvalerate, flucythrinate, flumethrin, fluvalinate (tau-); etofenprox, silafluofen; chlothianidin, dinotefuran, imidacloprid, nitenpyram, thiacloprid; spinosad, spinetoram; doramectin, eprinomectin, ivermectin, milbemycin oxime, moxidectin, selamectin; amitraz, cymiazole, demiditraz; piperonyl butoxide, and MGK264.

17. The combination according to claim 1, wherein A is 4-(7-bromo-1,3-benzodioxol-5-yl)-1-(3-methoxypyrazin-2-yl)-3-(trifluoromethyl)-1H-pyrazole-5-amine, and B is selected from the group consisting of: endosulphan (alpha-), lindane; fipronil, pyriprole; A1443; allethrin, bioallethrin, permethrin, phenothrin, resmethrin, tetramethrin; cyfluthrin (beta-), cyhalothrin (lambda-), cypermethrin (alpha-, zeta-), deltamethrin, fenvalerate, flucythrinate, flumethrin, fluvalinate (tau-); etofenprox, silafluofen; chlothianidin, dinotefuran, imidacloprid, nitenpyram, thiacloprid; spinosad, spinetoram; doramectin, eprinomectin, ivermectin, milbemycin oxime, moxidectin, selamectin; amitraz, cymiazole, demiditraz; piperonyl butoxide, and MGK264.

18. The combination according to claim 1, wherein A is 4-(7-bromo-1,3-benzodioxol-5-yl)-1-(3-ethoxypyrazin-2-yl)-3-ethyl-1H-pyrazole-5-amine, and B is selected from the group consisting of: endosulphan (alpha-), lindane; fipronil, pyriprole; A1443; allethrin, bioallethrin, permethrin, phenothrin, resmethrin, tetramethrin; cyfluthrin (beta-), cyhalothrin (lambda-), cypermethrin (alpha-, zeta-), deltamethrin, fenvalerate, flucythrinate, flumethrin, fluvalinate (tau-); etofenprox, silafluofen; chlothianidin, dinotefuran, imidacloprid, nitenpyram, thiacloprid; spinosad, spinetoram; doramectin, eprinomectin, ivermectin, milbemycin oxime, moxidectin, selamectin; amitraz, cymiazole, demiditraz; piperonyl butoxide, and MGK264.

19. The combination according to claim 1, wherein A is 4-(7-bromo-1,3-benzodioxol-5-yl)-1-(3-methoxypyrazin-2-yl)-3-ethyl-1H-pyrazole-5-amine, and B is selected from the group consisting of: endosulphan (alpha-), lindane; fipronil, pyriprole; A1443; allethrin, bioallethrin, permethrin, phenothrin, resmethrin, tetramethrin; cyfluthrin (beta-), cyhalothrin (lambda-), cypermethrin (alpha-, zeta-), deltamethrin, fenvalerate, flucythrinate, flumethrin, fluvalinate (tau-); etofenprox, silafluofen; chlothianidin, dinotefuran, imidacloprid, nitenpyram, thiacloprid; spinosad, spinetoram; doramectin, eprinomectin, ivermectin, milbemycin oxime, moxidectin, selamectin; amitraz, cymiazole, demiditraz; piperonyl butoxide, and MGK264.

20. The combination according to claim 1, wherein A is 1-(3-ethoxypyrazin-2-yl)-3-(triluoromethyl)-4-[7-(trifluoromethyl)-1,3-benzodioxol-5-yl]-1H-pyrazole-5-amine, and B is selected from the group consisting of: endosulphan (alpha-), lindane; fipronil, pyriprole; A1443; allethrin, bioallethrin, permethrin, phenothrin, resmethrin, tetramethrin; cyfluthrin (beta-), cyhalothrin (lambda-), cypermethrin (alpha-, zeta-), deltamethrin, fenvalerate, flucythrinate, flumethrin, fluvalinate (tau-); etofenprox, silafluofen; chlothianidin, dinotefuran, imidacloprid, nitenpyram, thiacloprid; spinosad, spinetoram; doramectin, eprinomectin, ivermectin, milbemycin oxime, moxidectin, selamectin; amitraz, cymiazole, demiditraz; piperonyl butoxide, and MGK264.

21. The combination according to claim 1, wherein A is 1-(3-methoxypyrazin-2-yl)-3-(triluoromethyl)-4-[7-(trifluoromethyl)-1,3-benzodioxol-5-yl]-1H-pyrazole-5-amine, and B is selected from the group consisting of: endosulphan (alpha-), lindane; fipronil, pyriprole; A1443; allethrin, bioallethrin, permethrin, phenothrin, resmethrin, tetramethrin; cyfluthrin (beta-), cyhalothrin (lambda-), cypermethrin (alpha-, zeta-), deltamethrin, fenvalerate, flucythrinate, flumethrin, fluvalinate (tau-); etofenprox, silafluofen; chlothianidin, dinotefuran, imidacloprid, nitenpyram, thiacloprid; spinosad, spinetoram; doramectin, eprinomectin, ivermectin, milbemycin oxime, moxidectin, selamectin; amitraz, cymiazole, demiditraz; piperonyl butoxide, and MGK264.

22. The combination according to claim 1, wherein A is 4-(3,5-dichloro-4-methoxyphenyl)-1-(3-ethoxypyrazin-2-yl)-3-(trifluoromethyl)-1H-pyrazole-5-amine; and, and B is selected from the group consisting of: endosulphan (alpha-), lindane; fipronil, pyriprole; A1443; allethrin, bioallethrin, permethrin, phenothrin, resmethrin, tetramethrin; cyfluthrin (beta-), cyhalothrin (lambda-), cypermethrin (alpha-, zeta-), deltamethrin, fenvalerate, flucythrinate, flumethrin, fluvalinate (tau-); etofenprox, silafluofen; chlothianidin, dinotefuran, imidacloprid, nitenpyram, thiacloprid; spinosad, spinetoram; doramectin, eprinomectin, ivermectin, milbemycin oxime, moxidectin, selamectin; amitraz, cymiazole, demiditraz; piperonyl butoxide, and MGK264.

23. The combination according to claim 1, wherein A is 4-[3,5-dichloro-4-(dimethylamino)phenyl]-1-(3-ethoxypyrazin-2-yl)-3-(trifluoromethyl)-1H-pyrazole-5-amine, and B is selected from the group consisting of: endosulphan (alpha-), lindane; fipronil, pyriprole; A1443; allethrin, bioallethrin, permethrin, phenothrin, resmethrin, tetramethrin; cyfluthrin (beta-), cyhalothrin (lambda-), cypermethrin (alpha-, zeta-), deltamethrin, fenvalerate, flucythrinate, flumethrin, fluvalinate (tau-); etofenprox, silafluofen; chlothianidin, dinotefuran, imidacloprid, nitenpyram, thiacloprid; spinosad, spinetoram; doramectin, eprinomectin, ivermectin, milbemycin oxime, moxidectin, selamectin; amitraz, cymiazole, demiditraz; piperonyl butoxide, and MGK264.

\* \* \* \* \*